US009603904B2

(12) United States Patent
Johansen et al.

(10) Patent No.: US 9,603,904 B2
(45) Date of Patent: Mar. 28, 2017

(54) TREATING DIABETES MELITUS USING INSULIN INJECTIONS WITH LESS THAN DAILY INJECTION FREQUENCY

(75) Inventors: Thue Johansen, Copenhagen Ø (DK); Birgitte Koch Michelsen, Lyngby (DK); Berit Edsberg, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 333 days.

(21) Appl. No.: 13/124,750

(22) PCT Filed: Oct. 29, 2009

(86) PCT No.: PCT/EP2009/064290
§ 371 (c)(1),
(2), (4) Date: May 27, 2011

(87) PCT Pub. No.: WO2010/049488
PCT Pub. Date: May 6, 2010

(65) Prior Publication Data
US 2011/0230402 A1 Sep. 22, 2011

Related U.S. Application Data

(60) Provisional application No. 61/109,703, filed on Oct. 30, 2008.

(30) Foreign Application Priority Data

Oct. 30, 2008 (EP) ..................... 08167990

(51) Int. Cl.
*A61P 3/10* (2006.01)
*A61K 38/28* (2006.01)
*A61K 38/22* (2006.01)
*C07K 14/575* (2006.01)
*C07K 14/62* (2006.01)
*A61K 45/06* (2006.01)

(52) U.S. Cl.
CPC .............. *A61K 38/28* (2013.01); *A61K 38/22* (2013.01); *A61K 45/06* (2013.01); *C07K 14/575* (2013.01); *C07K 14/62* (2013.01)

(58) Field of Classification Search
USPC ......................................................... 514/6.3
See application file for complete search history.

(56) References Cited

U.S. PATENT DOCUMENTS

| | | | |
|---|---|---|---|
| 3,528,960 A | 9/1970 | Haas | |
| 3,868,358 A | 2/1975 | Jackson | |
| 3,907,676 A | 9/1975 | Jorgensen | |
| 4,476,118 A | 10/1984 | Brange et al. | |
| 4,669,430 A | 6/1987 | Reinold et al. | |
| 4,876,322 A | 10/1989 | Budde et al. | |
| 4,983,658 A | 1/1991 | Kress et al. | |
| 5,177,058 A | 1/1993 | Dorschug | |
| 5,382,574 A | 1/1995 | Jorgensen | |
| 5,605,884 A | 2/1997 | Lee et al. | |
| 5,646,242 A | 7/1997 | Baker et al. | |
| 5,750,497 A | 5/1998 | Havelund et al. | |
| 5,830,999 A | 11/1998 | Dunn | |
| 5,866,538 A | 2/1999 | Norup et al. | |
| 5,898,067 A | 4/1999 | Balschmidt et al. | |
| 5,905,140 A | 5/1999 | Hansen | |
| 6,011,007 A | 1/2000 | Havelund et al. | |
| 6,174,856 B1 | 1/2001 | Langballe et al. | |
| 6,211,144 B1 | 4/2001 | Havelund | |
| 6,221,837 B1 | 4/2001 | Ertl et al. | |
| 6,251,856 B1 | 6/2001 | Markussen et al. | |
| 6,335,316 B1 | 1/2002 | Hughes et al. | |
| 6,451,762 B1 | 9/2002 | Havelund et al. | |
| 6,451,970 B1 | 9/2002 | Schaffer et al. | |
| 6,504,005 B1 * | 1/2003 | Fridkin et al. | ................ 530/303 |
| 6,531,448 B1 | 3/2003 | Brader | |
| 6,620,780 B2 | 9/2003 | Markussen et al. | |
| 6,652,886 B2 | 11/2003 | Ahn et al. | |
| 6,869,930 B1 | 3/2005 | Havelund et al. | |
| 7,229,964 B2 | 6/2007 | Markussen et al. | |
| 7,402,565 B2 | 7/2008 | Kjeldsen et al. | |
| 7,544,656 B2 | 6/2009 | Sabetsky | |
| 7,615,532 B2 | 11/2009 | Jonassen et al. | |
| 8,003,605 B2 | 8/2011 | Bayer et al. | |
| 8,067,362 B2 | 11/2011 | Kodra et al. | |
| 8,722,620 B2 | 5/2014 | Fynbo et al. | |
| 8,828,923 B2 | 9/2014 | Jonassen et al. | |
| 9,034,818 B2 | 5/2015 | Poulsen et al. | |
| 9,131,722 B2 | 9/2015 | Kim et al. | |
| 2002/0045731 A1 | 4/2002 | Schaffer et al. | |
| 2002/0155994 A1 | 10/2002 | Havelund et al. | |
| 2003/0004096 A1 | 1/2003 | Boderke | |
| 2003/0236196 A1 | 12/2003 | Kerwin et al. | |
| 2004/0006000 A1 | 1/2004 | Langkjaer | |
| 2004/0116345 A1 | 6/2004 | Besman et al. | |
| 2004/0138099 A1 | 7/2004 | Draeger | |
| 2005/0054818 A1 | 3/2005 | Brader et al. | |
| 2005/0074866 A1 | 4/2005 | Grancha et al. | |
| 2005/0222006 A1 | 10/2005 | Havelund et al. | |
| 2005/0232899 A1 | 10/2005 | Balwani et al. | |
| 2006/0183668 A1 | 8/2006 | Jonassen et al. | |

(Continued)

FOREIGN PATENT DOCUMENTS

AU 2011252127 B2 2/2014
CN 1829738 A 9/2006
(Continued)

OTHER PUBLICATIONS

Jonassen et al., Pharmaceutical Research (2006) vol. 23, No. 1, 49-55.*

(Continued)

*Primary Examiner* — Marcela M Cordero Garcia
*Assistant Examiner* — Catherine Mader
(74) *Attorney, Agent, or Firm* — Rosemarie R. Wilk-Orescan

(57) ABSTRACT

The present invention relates to an insulin derivative for the treatment of a condition or disease where administration of insulin will be of benefit, comprising administering, to a patient in need thereof, effective dosages of the insulin derivative, wherein said insulin derivative exhibits a prolonged profile of action and wherein said dosages are administered at intervals longer than 24 hours.

16 Claims, 3 Drawing Sheets

(56) References Cited

U.S. PATENT DOCUMENTS

| | | |
|---|---|---|
| 2008/0076705 A1 | 3/2008 | Kodra et al. |
| 2009/0137454 A1 | 5/2009 | Fynbo et al. |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |
| 2011/0301081 A1 | 12/2011 | Becker et al. |
| 2013/0261051 A1 | 10/2013 | Johansen |
| 2014/0328943 A1 | 11/2014 | Havelund et al. |
| 2015/0250857 A1 | 9/2015 | Andresen et al. |
| 2016/0058840 A1 | 3/2016 | Johansen et al. |
| 2016/0296602 A1 | 10/2016 | Johansen |

FOREIGN PATENT DOCUMENTS

| | | |
|---|---|---|
| CN | 101389650 A | 12/2006 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 894095 | 2/1997 |
| EP | 818204 A2 | 1/1998 |
| EP | 925792 A2 | 6/1999 |
| EP | 1153608 A1 | 11/2001 |
| EP | 884053 B1 | 10/2002 |
| EP | 1283051 A1 | 2/2003 |
| EP | 0785713 B1 | 9/2003 |
| EP | 1595544 | 11/2005 |
| EP | WO/2007/074133 * | 7/2007 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | B S38-5689 | 5/1963 |
| JP | 1254699 | 5/1979 |
| JP | 57-067548 A | 4/1982 |
| JP | 5026567 A | 2/1993 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521006 A | 11/2001 |
| JP | 2001-521904 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2006-511441 A | 4/2006 |
| JP | 2006-519253 | 8/2006 |
| JP | 2007-523881 | 8/2007 |
| JP | 2004-523589 A | 5/2008 |
| JP | 2009/522231 A | 6/2009 |
| JP | 4808785 | 11/2011 |
| JP | 4959005 B2 | 6/2012 |
| JP | 5331071 B2 | 10/2013 |
| RU | 2160118 C2 | 12/2000 |
| RU | 2164520 C2 | 3/2001 |
| RU | 2352581 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 97/31022 A1 | 8/1997 |
| WO | 98/02460 A1 | 1/1998 |
| WO | 98/05361 | 2/1998 |
| WO | 98/42367 A1 | 10/1998 |
| WO | 98/42368 A1 | 10/1998 |
| WO | 98/47529 A1 | 10/1998 |
| WO | 99/21888 A1 | 5/1999 |
| WO | 99/24071 A1 | 5/1999 |
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 01/49314 A2 | 7/2001 |
| WO | 02076495 A1 | 10/2002 |
| WO | 03/002136 A2 | 1/2003 |
| WO | 03/013573 | 2/2003 |
| WO | 03030829 A2 | 4/2003 |
| WO | 03/053339 A2 | 7/2003 |
| WO | 03/094951 A1 | 11/2003 |
| WO | 03/094956 A1 | 11/2003 |
| WO | 2004/039392 A2 | 5/2004 |
| WO | 2004/112828 A1 | 12/2004 |
| WO | 2005/005477 A2 | 1/2005 |
| WO | 2005/016365 A2 | 2/2005 |
| WO | WO 2005/012347 | 2/2005 |
| WO | 2005/021022 A2 | 3/2005 |
| WO | 2005/047508 A1 | 5/2005 |
| WO | 2005/063298 A1 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 2006/051103 A2 | 5/2006 |
| WO | 2006/053906 A1 | 5/2006 |
| WO | 2006/079019 A2 | 7/2006 |
| WO | 2006/082204 | 8/2006 |
| WO | 2006/082205 | 8/2006 |
| WO | 2007/041481 A1 | 4/2007 |
| WO | 2007/074133 A2 | 7/2007 |
| WO | 2007/096431 A1 | 8/2007 |
| WO | 2007/121256 A2 | 10/2007 |
| WO | 2007/128815 A1 | 11/2007 |
| WO | WO 2007/128817 | 11/2007 |
| WO | WO 2007/135117 | 11/2007 |
| WO | 2008/034881 A1 | 3/2008 |
| WO | 2008/152106 A1 | 12/2008 |
| WO | 2009/060071 A1 | 5/2009 |
| WO | 2009/063072 A2 | 5/2009 |
| WO | 2010/049488 A1 | 5/2010 |
| WO | 2011/141407 | 11/2011 |
| WO | 2011141407 A1 | 11/2011 |
| WO | 2012055967 A2 | 5/2012 |
| WO | 2013037754 A2 | 3/2013 |

OTHER PUBLICATIONS

Brange, J et al Diabetic Medicine Neutral Insulin Solutions Physically Stabilized by Addition of ZN2+ 1986 3 6 532-536.
Havelund, S et al. Pharmaceutical Research the Mechanism of Protraction of Insulin . . . 2004 21 8 1498-1504.
Jonassen, I. et al Pharmaceutical Research—2006 23 1 49-55.
Schlichtkrull, J Acta Chemica Scandinavica Insulin Crystals 1956 10 9 1455-1458.
Whittingham.J.L et al. Biochemistry Crystallographic and Solution . . . 2004 43-5987-5995.
Annual Review—Increation and Metabolism 2000 pp. 46-53.
Definition of Moiety From http://dictionary.reference.com/browse/moiety, 2010, pp. 1-3.

(56) References Cited

OTHER PUBLICATIONS

Heise, T. et al., "Towards Peakless, Reporducible and Long-Acting Insulins. An Assessment of the Basal Analogues Based on Isoglycaemic Clamp Studies," Diabetes Obes Metab, 2007, vol. 9, No. 5, pp. 648-659.

Hinds et al., "Pegylated Insulin in PLGA Microparticles. In Vivo and In Vitro Analysis," J Control Release, 2005, vol. 104, No. 3, pp. 447-460.

Nathan, D.M. et al., "Management for Hyperglycemia in Type 2 Diabetes Consensus Algorithm for the Initiation and Adjustment of Therapy," Diabetes Care, 2008, vol. 31, No. 1, pp. 173-175.

Vajo et al., "Genetically Engineered Insulin Analogs: Diabetes in the New Millenium," Pharmacological Reviews, 2000, vol. 52, No. 1, pp. 1-9.

Hinds et al., "PEGylated insulin in PLGA microparticles. In vivo and in vitro analysis," Journal of Controlled Release, 2005, vol. 104, No. 3, pp. 447-460.

Irie et al., "Pharmacokenetics and Pharmacodynamics of Single Dose Insulin Detemir, Long-Acting Soluble Insulin Analogue Compared to NPH Insulin in Patients with Type 1 Diabetes Mellitus," Journal of Clinical Therapeutics and Medicine, 2007, vol. 23, No. 5, pp. 349-356.

Machine Translation of JP 2007-523881, published Aug. 23, 2007.
Machine Translation of JP 2000-51554, published Nov. 21, 2000.
Machine Translation of JP 2006-519253, published Aug. 24, 2006.

Nathan, D. M. et al., "Management of Hyperglycemia in Type 2 Diabetes: A Consensus Algorithm for the Initiation and Adjustment of Therapy," Diabetes Care, 2008, vol. 31, No. 1, pp. 173-175.

Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.

Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.

Barnett, A. H., "A Review of Basal Insulins," Diabet Med, 2003, vol. 20, No. 11, pp. 873-885.

Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.

Heller. S R, Current Medical Research and Opinion, "Insulin Analogues", 2002, vol. 18, No. 1, pp. 40-47.

I. Jonassen et al., Diabetologia, "Insulin Degludec: Multi-Hexamer Formation is the Underlying Basis for This New Generation Ultra-Long Acting Basal Insulin", 2010, vol. 53, No. 1, pp. S388.

R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", 2010, vol. 53, No. 1, pp. S389.

Samuel et al. "Studies on the immunogenicity of protamines in humans and experimental animals by means of a micro-complement fixation test." Clin. Exp. Immunol. vol. 33: pp. 252-260. 1978.

Kurtz et al. "Circulating IgG antibody to protamine in patients treated with protamine-insulins." Diabetologica. vol. 25: pp. 322-324. 1983.

Defining and Reporting Hypoglycemia in Diabetes: A report from the American Diabetes Association Workgroup on Hypoglycemia, Diabetes Care, 2005, vol. 28, No. 5, pp. 1245-1249.

Humulin® R Regular U-500 (Concentrated), Insulin Human Injection, USP (rDNA Origin), Eli Lilly and Company, Lilly USA, LLC, Indianapolis, IN 46285, USA, 1996.

ICH Harmonised Tripartite Guideline: Guideline for Good Clinical Practice, Journal of postgraduate medicine, 2001, vol. 47, No. 3, pp. 199-203.

Marcus A., Diabetes care—insulin delivery in a changing world, The Medscape Journal of Medicine, 2008, vol. 10, No. 5, 120.

Anderson RM et al. Patient empowerment: results of a randomized controlled trial. Diabetes Care. 1995, vol. 18, No. 7 pp. 943-949.

Barnett et al: Dosing of insulin glargine in the treatment of type 2 diabetes ,Clinical Therapeutics, 2007 vol. 29, No. 6,,pp. 987-999.

Benjamin EM. Self-monitoring of blood glucose: the basics. Clinical Diabetes. 2002, vol. 20, No. 1, pp. 45-47.

Canadian Diabetes Association Clinical Practice Guidelines Expert Committee. Canadian Diabetes Association. Canadian Journal of Diabetes. 2008, vol. 32(Suppl 1)pp. S1-S201.

Davies M, et al.. Improvement of glycemic control in subjects with poorly controlled type 2 diabetes. Diabetes Care. 2005,vol. 28, No. 6, pp. 1282-1288.

Deutsch T et al,Utopia: A Consultation System for Visit-By-Visit Diabetes Management, Medical Informatica. Taylor and Francis.; Basingstoke. GB, 1996, vol. 21, No. 4, pp. 345-358.

Gerstein H C et al. A randomized trial of adding insulin glargine vs.avoidance of insulin in people with Type 2 diabetes on either no oral glucose-lowering agents or submaximal doses of metformin and/or sulphonylureas. The Canadian Insight (Implementing New Strategies with Insulin Glargine for Hyperglycaemia treatment) Study, Diabetic Medicines, 2006, vol. 23, No. 7, pp. 736-742.

Holman RR et al.,10-Year Follow-up of Intensive Glucose Control in Type 2 Diabetes,The New England Journal of Medicine, 2008, vol. 359, pp. 1577-1589.

Holman RR et al.A practical guide to Basal and Prandial Insulin therapy, Diabetic Medicine, 1985, vol. 2, pp. 45-53.

International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.

Janka Hans U et al, Combination of oral antidiabetic agents with basal insulin; versus premixed insulin alone in randomized elderly patients with type 2 diabetes mellitus, Journal of the American Geriatrics Society, 2007,vol. 55, No. 2, pp. 182-188.

Kulzer B, et al. Effects of self-management training in type 2 diabetes: a randomized, prospective trial. Diabetic Medicine. 2007, vol. 24, No. 4, pp. 415-423.

Lantus® (insulin glargine [rDNA origin] injection). sanofi-aventis U.S. LLC, Bridgewater, NJ, USA; 2007. Health Care Professional. Dosing & Titration. Available at: http://www.lantus.com/hcp/titration.aspx. Accessed Nov. 13, 2012.

Liebl A, et al. Direct costs and health-related resource utilisation in the 6 months after insulin initiation in German patients with type 2 diabetes mellitus in 2006: Instigate study. Current Medical Research Opinion 2008,vol. 24, No. 3, pp. 2349-2358.

Meneghini L et al., The usage of a simplified self-titration dosing guideline (303 Algorithm) for insulin detemir in patients with type 2 diabetes-results of the randomized, controlled Predictive TM 303 study. Diabetes Obesity and Metabolism. 2007, vol. 9, pp. 902-913.

Nathan DM et al,Intensive Diabetes Treatment and Cardiovascular Disease in Patients with Type 1 Diabetes,The new england journal of medicine, 2005, vol. 353, No. 25, pp. 2643-2653.

Nathan DM et al.Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.

Nathan DM et al.The Effect of Intensive Treatment of Diabetes on the Development and Progression of Long-Term Complications in Insulin-Dependent Diabetes Mellitus,The Diabetes Control and Complications Trial Research Group,The New England Journal of medicine, 1993, vol. 329, No. 14, pp. 977-986.

Norris SL, et al. Self-management education for adults with type 2 diabetes: a meta-analysis on the effect of glycemic control. Diabetes Care, 2002, vol. 25, No. 7, pp. 1159-1171.

Ohkubo Y et al. Intensive insulin therapy prevents the progression of diabetic microvascular complications in Japanese patients with non-insulin-dependent diabetes mellitus: a randomized prospective 6-year study,Diabetes Research and Clinical Practice, 1995, vol. 28, No. 2 pp. 103-117.

Selvin E et al,.Meta-Analysis: Glycosylated Hemoglobin and Cardiovascular Disease in; Diabetes Mellitus, Annals of internal medicine,2004, vol. 141, pp. 421-431.

(56) References Cited

OTHER PUBLICATIONS

The ADVANCE Collaborative Group, Patel A et al.Intensive Blood Glucose Control and Vascular Outcomes in Patients with Type 2 Diabetes, The new England Journal of Medicine, 2008, vol. 358, pp. 2560-2572.
UK Prospective Diabetes Study (UKPDS) Group, Intensive blood-glucose control with sulphonylureas or insulin compared with conventional treatment and risk of complications in patients with type 2 diabetes (UKPDS 33)., Lancet, 1998, vol. 352 (9131), pp. 837-853.
American Diabetes Association. Insulin administration. Diabetes Care. 2002 vol. 25: pp. S112-S115.
World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.
International Conference on Harmonisation. ICH Harmonised Tripartite Guideline:Guideline for Good Clinical Practice. E6 (R1), Sep 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.
Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.
Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.
Rubin RR et al.. Factors affecting use of insulin pens by patients with type 2 diabetes. Diabetes Care. 2008 vol. 31 pp. 430-432.
Anthony H. Barnett, Diabetic Medicine, A Review of Basal Insulins, 2003, vol. 20, No. 11, pp. 873-885.
Heise, T. et al., Diabetes, Obesity and Metabolism, Towards Peakless, Reproducible and Long-Acting Insulins. An Assessment of the Basal Analogues Based on Isoglycaemic Clamp Studies, 2007, vol. 9, No. 5, pp. 648-659.
IDF Clinical Guidelines Task Force, Brussels: International Diabetes Federation 2005, Global Guideline for Type 2 Diabetes, 2005.
IDF Clinical Guidelines Task Force, Brussels: International Diabetes Federation 2007, Guideline for Management of Postmeal Glucose, 2007.
Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.
Heise et al "Lower Within-Subject Variability of Insulin Detemir in Comparison to NPH Insulin an Insulin Glargine in People with Type 1 Diabetes" Diabetes, 2004, vol. 53, pp. 1614-1620.
Novo Nordisk, Levemir Product Information, Jun. 16, 2005. 42 pages.
Talboys Catalog, 2008 Laboratory Equipment Catalog, Talboys by Troemner, 122 pages (2008).

* cited by examiner

1

TREATING DIABETES MELITUS USING INSULIN INJECTIONS WITH LESS THAN DAILY INJECTION FREQUENCY

CROSS-REFERENCE TO RELATED APPLICATIONS

This application is a 35 U.S.C. §371 national stage application of International Patent Application PCT/EP2009/064290 (published as WO 2010/049488), filed Oct. 29, 2009, which claimed priority of European Patent Applications 08167990.4, filed Oct. 30, 2008; this application further claims priority under 35 U.S.C. §119 of U.S. Provisional Application 61/109,703, filed Oct. 30, 2008.

FIELD OF THE INVENTION

The present invention relates to a novel insulin administration scheme, which is i.a. useful in treatment of diabetes mellitus and hyperglycaemia, in particular of insulin-dependent diabetes mellitus. The administration of insulin and insulin involves use of analogues having a prolonged profile of action in a novel dosage regimen.

BACKGROUND OF THE INVENTION

Diabetes mellitus often requires insulin treatment to establish proper metabolic control (comprising mainly glycaemic control, but also other metabolic parameters benefit from insulin treatment). The established practise of insulin treatment is to administer the insulin product once or more often per day, optionally in combination with other treatment modalities, as described in available treatment guidelines. Intravenous and subcutaneous insulin infusion is also used in clinical practise.

One widely used insulin treatment option is to administer a long acting insulin product, also referred to as basal insulin, to cover the insulin need of the patient wholly or partially. The long acting insulin is administered once or more often per day and is used on both Diabetes type 1 and type 2 as well as for other forms of insulin requiring disease states (hyperglycaemia of any cause).

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

The current practice in management of diabetes and hyperglycaemia is set forth in e.g.:

IDF Clinical Guidelines Task Force. Global Guideline for Type 2 Diabetes. *Brussels: International Diabetes Federation*, 2005, http://www.idf.org/webdata/docs/IDF%20GGT2D.pdf, IDF Clinical Guidelines Task Force. Guideline for Management of PostMeal Glucose. *Brussels: International Diabetes Federation*, 2007, http://www.idf.org/webdata/docs/Guideline_PMG_final.pdf, D. M. Nathan, J. B. Buse, M. B. Davidson, E. Ferrannini, R. R. Holman, R. Sherwin, and B. Zinman. Management of hyperglycemia in type 2 diabetes: a consensus algorithm for the initiation and adjustment of therapy: update regarding thiazolidinediones: a consensus statement from the American Diabetes Association and the European Association for the Study of Diabetes. *Diabetes care* 31 (1):173-175, 2008, Reviews relating to basic insulin analogues and their characteristics and current clinical use can i.a. be found in:

T. Heise and T. R. Pieber. Towards peakless, reproducible and long-acting insulins. An assessment of the basal analogues based on isoglycaemic clamp studies. *Diabetes Obes Metab* 9 (5):648-659, 2007, and A. H. Barnett. A review of basal insulins. *Diabet Med* 20 (11):873-885, 2003.

DESCRIPTION OF THE INVENTION

Figure 1:
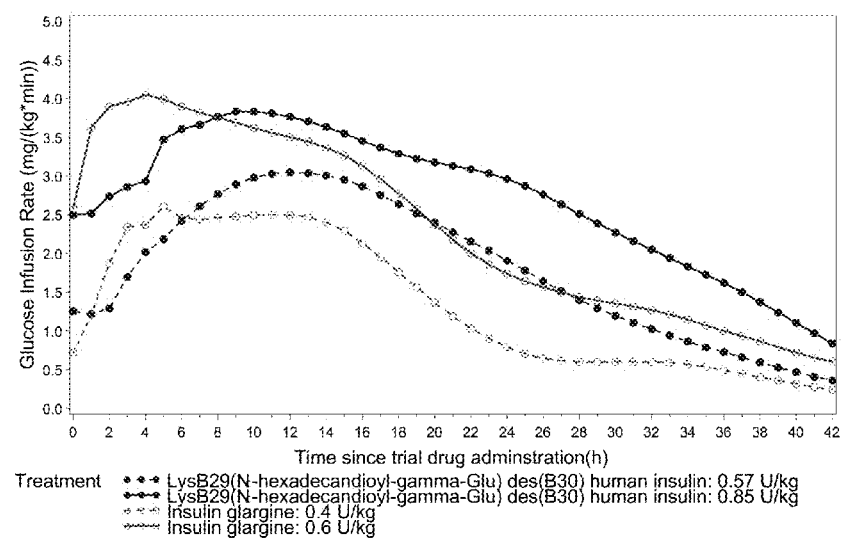
FIG. 1 shows the glucose infusion rate plotted against the time since the administration of the trial drug.

The present invention is based on the surprising finding that it is possible to treat diabetes and hyperglycaemia by administration of insulin at increased intervals. For instance it has been verified that intervals longer than 24 hours provide for satisfactory diabetes treatment regimens. A number of advantages directly follow from such simplified treatment regimens:

Convenience is improved for patients by the less than daily administration need

Less than bi-daily administration during part of the week further improves convenience Improved convenience potentially improves patient compliance ultimately improving the long term outcome for the patient If an administration device is used to administer less than daily lower cost of treatment may result from lower needle or device auxiliary component consumption.

In its most general aspect, the invention hence relates to a method for treatment of a condition or disease where administration of insulin will be of benefit, comprising administering, to a patient in need thereof, effective dosages of an insulin derivative of a naturally occurring insulin or an insulin analogue, wherein said insulin derivative exhibits a prolonged profile of action and wherein said dosages are administered at intervals longer than 24 hours.

The invention also relates to use of such insulin derivatives in treatment methods discussed herein, and the invention also relates to use of such insulin derivatives in preparation of pharmaceutical compositions for the treatment of the diseases and conditions discussed herein.

Diseases and conditions which are the primary targets for this method are diabetes mellitus (type 1 or 2) or other conditions characterized by hyperglycaemia, but also metabolic diseases and conditions in general where the metabolic effects of insulin has a clinical relevance are of interest, such as pre-diabetes, impaired glucose tolerance, metabolic syndrome, obesity, cachexia, in vivo beta-cell loss/death, excessive appetite, and inflammation. All these types of conditions are known to or believed to benefit from a stable metabolic state in the subject who has the disease/condition.

At any rate, any therapeutic regimen where administration of insulin is included may be modified by implementing the current teachings, meaning that such therapies will include administration of prolonged-profile-of-action insulins, insulin analogues or derivatives of either of these according to the teachings provided herein.

Treatment Regimens of the Invention

The invention is best used at the convenience of the patient. Therefore, specific administration intervals will be explored for each insulin product exhibiting a sufficiently long profile of action to allow for the presently disclosed dosage regimens where dosages are administered less than daily. The final mode of use thus depends both on the product's capabilities and on the disposition and preference of the patient. This is due to the fact that the effect of any insulin depends on the insulin need of the individual patient and the sensitivity to the pharmacodynamic actions of insulin and lastly also to the preferences of the patient in a given situation. These conditions may change over time, both in terms of longer periods (years) and from day to day.

Nevertheless, the present invention provides a number of embodiments of a general dosage regimen.

In one embodiment of the method of the invention, the dosages are administered at intervals of at least 36 hours. In one embodiment of the method of the invention, the dosages are administered at intervals of at least 42 hours. The intervals may be longer, depending i.a. on the duration of the prolonged action of the insulin, analogue or derivative used. So, in some embodiment said dosages are administered at intervals of at least 48 hours, in other embodiments said dosages are administered at intervals of at least 72 hours, in a further embodiment said dosages are administered at intervals of at least 96 hours, and in yet one further embodiment said dosages are administered at intervals of at least 120 hours.

In other embodiment, said dosages are administered at intervals of at least 144 hours, but higher intervals may according to the invention be employed, meaning that said dosages may be administered at intervals of at least 168 hours, and even as high intervals as at most 336 hours constitute an embodiment of the present invention.

In an embodiment said dosages are administered at intervals of at most 312 hours.

In another embodiment said dosages are administered at intervals of at most 288 hours.

In yet another embodiment said dosages are administered at intervals of at most 264 hours.

In a further embodiment said dosages are administered at intervals of at most 240 hours.

In yet one further embodiment, said dosages are administered at intervals of at most 216 hours.

One embodiment entails that said dosages are administered at intervals of at most 192 hours, and another embodiment entails that said dosages are administered at intervals of at most 168 hours.

In one line of embodiments of the invention the dosages are administered at regular intervals. For instance, said dosages are in one of these embodiments administered every second day. In another of these embodiments said dosages are administered every third day, and in yet another of these embodiments, said dosages are administered every 4th day. Other embodiments include those where said dosages are administered every 5th day, where said dosages are administered every 6th day, where said dosages are administered every 7th day and those where said dosages are administered every 14th day—however, the invention also includes those embodiments, where said dosages are administered every 8th, 9th, 10th, 11th, 12th, or 13th day.

As an alternative to administration of at regular intervals it is an embodiment of the invention that the dosages are administered at fixed weekdays. This entails an advantage seen from patient perspective for the simple reason that it is easier to memorize a fixed weekly scheme.

Hence in one embodiment the dosages are administered at 3 fixed weekdays. In another embodiment the dosages are administered at 2 fixed weekdays.

In one embodiment none of said fixed weekdays are adjacent to each other. For an administration scheme including 3 weekdays, this means that the following schemes are possible: Monday-Wednesday-Friday; Monday-Wednesday-Saturday; Monday-Thursday-Saturday; Tuesday-Thursday-Saturday; Tuesday-Thursday-Sunday; and Tuesday-Friday-Sunday.

In the embodiment using 2 fixed weekdays, these are according to a more specific embodiment separated by 2 and 3 other weekdays—i.e. allowing for the following schemes: Monday-Thursday; Monday-Friday; Tuesday-Friday; Tuesday-Saturday; Wednesday-Saturday; Wednesday-Sunday; and Thursday-Sunday.

The method according to any one of the claims, wherein substantially no other naturally occurring insulin, insulin analogue or derivative of naturally occurring insulin or insulin analogue is administered to said patient.

Insulins with Prolonged Action Useful in the Invention

Interesting derivatives with prolonged profiles of action are disclosed in WO 2005/012347 (Novo Nordisk) and these are all considered especially useful for putting the present invention into practice—in the following, these are termed "the '347 derivatives".

Use of '347 Derivative in the Method of the Invention

The method of the invention include embodiments where the derivative is a '347 derivative, i.e. a derivative of a naturally occurring insulin or an insulin analogue has a side chain attached either to the α-amino group of the N-terminal amino acid residue of the B chain or to the ε-amino group of a Lys residue present in the B chain of the parent insulin, the side chain being of the general formula:

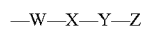

wherein W is:

an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:

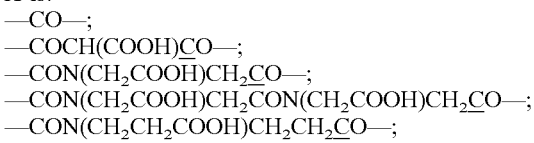

—CON(CH$_2$CH$_2$COOH)CH$_2$CH$_2$CON(CH$_2$CH$_2$COOH)CH$_2$CH$_2$C̲O̲—;
  —CONHCH(COOH)(CH$_2$)$_4$NHC̲O̲—;
  —CON(CH$_2$CH$_2$COOH)CH$_2$C̲O̲—; or
  —CON(CH$_2$COOH)CH$_2$CH$_2$C̲O̲—.
  that
  a) when W is an amino acid residue or a chain of amino acid residues, via a bond from the underscored carbonyl carbon forms an amide bond with an amino group in W, or
  b) when W is a covalent bond, via a bond from the underscored carbonyl carbon forms an amide bond with the N-terminal α-amino group in the B chain or with the ε-amino group of a Lys residue present in the B chain of the parent insulin;
  Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32;
  a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and
  Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H;
  and any Zn$^{2+}$ complexes thereof, provided that when W is a covalent bond and X is —CO—, then Z is different from —COOH.

In one embodiment the side chain —W—X—Y—Z is attached to the α-amino group of the N-terminal amino acid residue of the B chain of the parent insulin.

In another embodiment of the invention, side chain —W—X—Y—Z is attached to the ε-amino group of a Lys residue present in the B chain of the parent insulin. In one more specific aspect of this embodiment, the side chain —W—X—Y—Z is attached to the ε-amino group of a Lys residue present in position 28 of the B chain. In a further more specific aspect of this embodiment, the side chain —W—X—Y—Z is attached to the ε-amino group of a Lys residue present in position 29 of the B chain. In a further more specific aspect of this embodiment, the side chain —W—X—Y—Z is attached to the ε-amino group of a Lys residue present in position 30 of the B chain.

The substructure W of the side chain —W—X—Y—Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, β-Asp, α-Glu, and γ-Glu. Further options for W are for example α-hGlu and δ-hGlu.

In a further embodiment, W is a chain composed of two α-amino acid residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In a further embodiment, W is a chain composed of three α-amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one embodiment, the amino acid residues are codable residues.

In a further embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In one embodiment W can be connected to the ε-amino group of the Lys residue in the B-chain via an urea derivative.

The substructure X of the side chain —W—X—Y—Z can be a group of the formula —C̲O̲— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CH(COOH)C̲O̲— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$C̲O̲— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$C̲O̲— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$CH$_2$CO— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$CON(CH$_2$COOH)CH$_2$CO— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$CO— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$CON(CH$_2$CH$_2$COOH)CH$_2$CH$_2$CO— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

The substructure Y of the side chain —W—X—Y—Z can be a group of the formula —(CH$_2$)$_m$— where m is an integer in the range of from 6 to 32, from 8 to 20, from 12 to 20, or from 12-16.

In another embodiment, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In another embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In one embodiment, the substructure Z of the side chain —W—X—Y—Z is —COOH provided that when W is a covalent bond and X is —CO—, then Z is different from —COOH.

In another embodiment, Z is —CO-Asp.
In another embodiment, Z is —CO-Glu.
In another embodiment, Z is —CO-Gly.
In another embodiment, Z is —CO-Sar.
In another embodiment, Z is —CH(COOH)$_2$.
In another embodiment, Z is —N(CH$_2$COOH)$_2$.
In another embodiment, Z is —SO$_3$H.
In another embodiment, Z is —PO$_3$H.

In a further embodiment W is selected from the group consisting of α-Asp, β-Asp, α-Glu, and γ-Glu; X is —CO— or —CH(COOH)CO; Y is —(CH$_2$)$_m$— where m is an integer in the range of 12-18 and Z is —COOH or —CH(COOH)$_2$.

The insulin moiety—in the present text also referred to as the parent insulin—of a '347 derivative can be a naturally occurring insulin such as human insulin or porcine insulin. Alternatively, the parent insulin can be an insulin analogue.

In one group of parent insulin analogues, the amino acid residue at position A21 is Asn.

In another group of parent insulin analogues, the amino acid residue at position A21 is Gly. Specific examples from this group of analogues are Gly$^{A21}$ human insulin, Gly$^{A21}$ des(B30) human insulin; and Gly$^{A21}$Arg$^{B31}$Arg$^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is Asp$^{B28}$ human insulin.

In another group of parent insulin analogues, the amino acid residue at position B28 is Lys and the amino acid residue at position B29 is Pro. A specific example from this group of parent insulin analogues is Lys$^{B28}$Pro$^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is Thr$^{B29}$Lys$^{B30}$ human insulin.

In another group of parent insulin analogues, the amino acid residue at position B3 is Lys and the amino acid residue at position B29 is Glu. A specific example from this group of parent insulin analogues is Lys$^{B3}$Glu$^{B29}$ human insulin.

Examples of '347 derivatives useful in the invention are the following compounds:

N$^{εB29}$—(N$^α$—(HOOC(CH$_2$)$_{14}$CO)-γ-Glu) des(B30) human insulin;
N$^{εB29}$—(N$^α$—(HOOC(CH$_2$)$_{15}$CO)-γ-Glu) des(B30) human insulin;
N$^{εB29}$—(N$^α$—(HOOC(CH$_2$)$_{16}$CO)-γ-Glu) des(B30) human insulin;
N$^{εB29}$—(N$^α$—(HOOC(CH$_2$)$_{17}$CO)-γ-Glu) des(B30) human insulin;
N$^{εB29}$—(N$^α$—(HOOC(CH$_2$)$_{18}$CO)-γ-Glu) des(B30) human insulin;
N$^{εB29}$—(N$^α$—(HOOC(CH$_2$)$_{16}$CO)-γ-Glu-N-(γ-Glu)) des(B30) human insulin;
N$^{εB29}$—(N$^α$-(Asp-OC(CH$_2$)$_{16}$CO)-γ-Glu) des(B30) human insulin;
N$^{εB29}$—(N$^α$-(Glu-OC(CH$_2$)$_{14}$CO)-γ-Glu) des(B30) human insulin;
N$^{εB29}$—(N$^α$-(Glu-OC(CH$_2$)$_{14}$CO—) des(B30) human insulin;
N$^{εB29}$—(N$^α$-(Asp-OC(CH$_2$)$_{16}$CO—) des(B30) human insulin;
N$^{εB29}$—(N$^α$—(HOOC(CH$_2$)$_{16}$CO)-α-Glu-N-(β-Asp)) des(B30) human insulin;
N$^{εB29}$—(N$^α$-(Gly-OC(CH$_2$)$_{13}$CO)-γ-Glu) des(B30) human insulin;
N$^{εB29}$—(N$^α$-(Sar-OC(CH$_2$)$_{13}$CO)-γ-Glu) des(B30) human insulin;
N$^{εB29}$—(N$^α$—(HOOC(CH$_2$)$_{13}$CO)-γ-Glu) des(B30) human insulin;
N$^{εB29}$—(N$^α$—(HOOC(CH$_2$)$_{13}$CO)-β-Asp) des(B30) human insulin;

$N^{\epsilon B29}$—($N^{\alpha}$—(HOOC(CH$_2$)$_{13}$CO)-α-Glu) des(B30) human insulin;

$N^{\epsilon B29}$—($N^{\alpha}$—(HOOC(CH$_2$)$_{16}$CO)-γ-D-Glu) des(B30) human insulin;

$N^{\epsilon B29}$—($N^{\alpha}$—(HOOC(CH$_2$)$_{14}$CO)-β-D-Asp) des(B30) human insulin;

$N^{\epsilon B29}$—(N—HOOC(CH$_2$)$_{16}$CO-β-D-Asp) des(B30) human insulin;

$N^{\epsilon B29}$—(N—HOOC(CH$_2$)$_{14}$CO-IDA) des(B30) human insulin;

$N^{\epsilon B29}$—[N—(HOOC(CH$_2$)$_{16}$CO)—N-(carboxyethyl)-Gly] des(B30) human insulin;

$N^{\epsilon B29}$—[N—(HOOC(CH$_2$)$_{14}$CO)—N-(carboxyethyl)-Gly] des(B30) human insulin; and $N^{\epsilon B29}$—[N—(HOOC(CH$_2$)$_{14}$CO)—N-(carboxymethyl)-β-Ala] des(B30) human insulin.

'347 derivatives may be provided in the form of essentially zinc free compounds or in the form of zinc complexes. When zinc complexes of a '347 derivative are provided, two $Zn^{2+}$ ions, three $Zn^{2+}$ ions or four $Zn^{2+}$ ions can be bound to each insulin hexamer. Solutions of zinc complexes of the insulin derivatives will contain mixtures of such species.

Details pertaining to the preparation, formulation, pharmacology and other characteristics of relevance for the '347 derivatives are set forth in WO 2005/012347, which is hereby incorporated by reference herein.

Rapid Acting Insulin Analogues

Embodiments of the method of the invention include those wherein administration of the naturally occurring insulin, insulin analogue or derivative exhibiting a prolonged profile of action is supplemented with more frequent administrations of a fast-acting naturally occurring insulin, insulin analogue or derivative and/or administration of a non-insulin anti-diabetic drug.

So, one embodiment the invention provides a combination treatment, where any suitable insulin, analogue or derivative described above (e.g. $N^{\epsilon B29}$—($N^{\alpha}$—(HOOC(CH$_2$)$_{14}$CO)-γ-L-Glu) des(B30) human insulin=LysB29 (Nε-hexadecandioyl-γ-Glu) des(B30) human insulin (Example 4 in WO 2005/012347)) and a rapid acting insulin analogue are used in combination, e.g. in a combined product, but also administered separately. Hence, all specific disclosures in the present application which provide details relating to insulins useful in the presently disclosed invention relate mutatis mutandis to combination therapy involving the same compounds together with rapid acting insulin analogues. Typically, the rapid acting insulin is selected from the group consisting of $Asp^{B28}$ human insulin; $Lys^{B28}Pro^{B29}$ human insulin and $Lys^{B3}Glu^{B29}$ human insulin. The combined product shows no blunting. The insulin derivative disclosed in WO2005/012347 can be formulated with rapid acting insulin analogues as described in WO2007/074133, which is hereby incorporated by reference.

In one embodiment the invention provides a combination treatment with $N^{\epsilon B29}$—($N^{\alpha}$—(HOOC(CH$_2$)14CO)-γ-L-Glu) des(B30) human insulin and AspB28 human insulin together with pharmaceutically acceptable carriers and additives.

The insulin derivative according to the invention and the rapid acting insulin analogue can if necessary be mixed in a ratio from about 90/10%; about 80/20%, about 70/30%, about 60/40%, about 50/50%, about 40/60%, about 30/60%, about 20/80% or about 10/90%.

Other Combinations

In one embodiment of method of the invention, administration of the naturally occurring insulin, insulin analogue or derivative exhibiting a prolonged profile of action is supplemented with administration of a non-insulin anti-diabetic drug, such as metformin.

The invention is summarized in the following paragraphs:

1. An insulin derivative for the treatment of a condition or disease where administration of insulin will be of benefit, comprising administering, to a patient in need thereof, effective dosages of the insulin derivative, wherein said insulin derivative exhibits a prolonged profile of action and wherein said dosages are administered at intervals longer than 24 hours.

2. The insulin derivative according to embodiment 1, wherein said dosages are administered at intervals of at least 36 hours.

3. The insulin derivative according to embodiment 2, wherein said dosages are administered at intervals of at least 48 hours.

4. The insulin derivative according to embodiment 3, wherein said dosages are administered at intervals of at least 72 hours.

5. The insulin derivative according to embodiment 4, wherein said dosages are administered at intervals of at least 96 hours.

6. The insulin derivative according to embodiment 5, wherein said dosages are administered at intervals of at least 120 hours.

7. The insulin derivative according to embodiment 6, wherein said dosages are administered at intervals of at least 144 hours.

8. The insulin derivative according to embodiment 7, wherein said dosages are administered at intervals of at least 168 hours.

9. The insulin derivative according to any one of the preceding embodiments, wherein said dosages are administered at intervals of at most 336 hours.

10. The insulin derivative according to any one of the preceding embodiments, wherein said dosages are administered at intervals of at most 312 hours.

11. The insulin derivative according to any one of the preceding embodiments, wherein said dosages are administered at intervals of at most 288 hours.

12. The insulin derivative according to any one of the preceding embodiments, wherein said dosages are administered at intervals of at most 264 hours.

13. The insulin derivative according to any one of the preceding embodiments, wherein said dosages are administered at intervals of at most 240 hours.

14. The insulin derivative according to any one of the preceding embodiments, wherein said dosages are administered at intervals of at most 216 hours.

15. The insulin derivative according to any one of the preceding embodiments, wherein said dosages are administered at intervals of at most 192 hours.

16. The insulin derivative according to any one of the preceding embodiments, wherein said dosages are administered at intervals of at most 168 hours.

17. The insulin derivative according to any one of the preceding embodiments, wherein the dosages are administered at regular intervals.

19. The insulin derivative according to embodiment 17, wherein said dosages are administered every second day.

19. The insulin derivative according to embodiment 17, wherein said dosages are administered every third day.

20. The insulin derivative according to embodiment 17, wherein said dosages are administered every 4th day.

21. The insulin derivative according to embodiment 17, wherein said dosages are administered every 5th day.

22. The insulin derivative according to embodiment 17, wherein said dosages are administered every 6th day.
23. The insulin derivative according to embodiment 17, wherein said dosages are administered every 7th day.
24. The insulin derivative according to embodiment 17, wherein said dosages are administered every 14th day
25. The insulin derivative according to any one of embodiments 1-16, wherein the dosages are administered at fixed weekdays.
26. The insulin derivative according to embodiment 25, wherein the dosages are administered at 3 fixed weekdays.
27. The insulin derivative according to embodiment 25, wherein the dosages are administered at 2 fixed weekdays.
28. The insulin derivative according to embodiment 26 or 27, wherein none of said fixed weekdays are adjacent to each other.
29. The insulin derivative according to embodiment 27, wherein said 2 fixed weekdays are separated by 2 and 3 other weekdays.
30. The insulin derivative according to any one of the preceding embodiments, wherein administration of the insulin derivative exhibiting a prolonged profile of action is supplemented with more frequent administrations of a fast-acting naturally occurring insulin or insulin analogue and/or administration of a non-insulin anti-diabetic drug.
31. The insulin derivative according to any one of embodiments 1-29, wherein substantially no other naturally occurring insulin, insulin analogue or derivative of naturally occurring insulin or insulin analogue is administered to said patient.
32. The insulin derivative according to embodiment 31, wherein administration of the insulin derivative exhibiting a prolonged profile of action is supplemented administration of a non-insulin anti-diabetic drug.
33. The insulin derivative according to any one of the preceding embodiments, wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to the α-amino group of the N-terminal amino acid residue of the B chain or to the ε-amino group of a Lys residue present in the B chain of the parent insulin;
X is:
—CO—;
—COCH(COOH)<u>C</u>O—;
—CON(CH$_2$COOH)CH$_2$<u>C</u>O—;
—CON(CH$_2$COOH)CH$_2$CON(CH$_2$COOH)CH$_2$<u>C</u>O—;
—CON(CH$_2$CH$_2$COOH)CH$_2$CH$_2$<u>C</u>O—;
—CON(CH$_2$CH$_2$COOH)CH$_2$CH$_2$CON(CH$_2$CH$_2$COOH) CH$_2$CH$_2$<u>C</u>O—;
—CONHCH(COOH)(CH$_2$)$_4$NH<u>C</u>O—;
—CON(CH$_2$CH$_2$COOH)CH$_2$<u>C</u>O—; or
—CON(CH$_2$COOH)CH$_2$CH$_2$<u>C</u>O—
that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;
Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and
Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof, provided that when W is a covalent bond and X is —CO—, then Z is different from —COOH.
34. The insulin derivative according to embodiment 33, wherein side chain —W—X—Y—Z is attached to the α-amino group of the N-terminal amino acid residue of the B chain of the parent insulin.
35. The insulin derivative according to embodiment 33, wherein side chain —W—X—Y—Z is attached to the ε-amino group of a Lys residue present in the B chain of the parent insulin.
36. The insulin derivative according to any one of embodiments 33-35, wherein W is a covalent bond.
37. The insulin derivative according to any one of embodiments 33-35, wherein W is an α-amino acid residue having from 4 to 10 carbon atoms.
38. The insulin derivative according to embodiment 37, wherein W is selected from the group consisting of α-Asp, β-Asp, α-Glu, γ-Glu, α-hGlu and δ-hGlu.
39. The insulin derivative according to any one of embodiments 33-35, wherein W is a chain composed of two α-amino acid residues of which one has from 4 to 10 carbon atoms and a free carboxylic acid group while the other has from 2 to 11 carbon atoms but no free carboxylic acid group.
40. The insulin derivative according to embodiment 39, wherein W is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

41. The insulin derivative according to any one of embodiments 33-35, wherein W is a chain composed of two α-amino acid residues, independently having from 4 to 10 carbon atoms, and both having a free carboxylic acid group.
42. The insulin derivative according to embodiment 41, wherein W is selected from the group consisting of α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and 5-hGlu-5-hGlu.
43. The insulin derivative according to any one of embodiments 33-42, wherein X is —CO— or —CH(COOH)CO—.
44. The insulin derivative according to any one of embodiments 33-43, wherein X is
—CON(CH$_2$COOH)CH$_2$CO—;
—CON(CH$_2$COOH)CH$_2$CON(CH$_2$COOH)CH$_2$CO—;
—CON(CH$_2$CH$_2$COOH)CH$_2$CH$_2$CO—;
—CON(CH$_2$CH$_2$COOH)CH$_2$CH$_2$CON(CH$_2$CH$_2$COOH)CH$_2$CH$_2$CO—
—CON(CH$_2$CH$_2$COOH)CH$_2$CO—; or
—CON(CH$_2$COOH)CH$_2$CH$_2$CO—.
45. The insulin derivative according to any one of embodiments 33-44, wherein Y is —(CH$_2$)$_m$— where m is an integer in the range of from 6 to 32, from 8 to 20, from 12 to 20 or from 12-16.
46. The insulin derivative according to any one of embodiments 33-45, wherein Z is —COOH.
47. The insulin derivative according to any one of embodiments 33-45, wherein Z is —CH(COOH)$_2$.
48. The insulin derivative according to any one of embodiments 33-45, wherein Z is —N(CH$_2$COOH)$_2$.
49. The insulin derivative according to any one of embodiments 33-45, wherein Z is —SO$_3$H.
50. The insulin derivative according to any one of embodiments 33-45, wherein Z is —PO$_3$H.
51. The insulin derivative according to any one of embodiments 33-50, wherein the parent insulin has Asn or Gly at position A21.
52. The insulin derivative according to any one of embodiments 33-50, wherein the parent insulin is a des(B1) analogue.
53. The insulin derivative according to any one of embodiments 33-50, wherein the parent insulin is a des(B30) analogue.
54. The insulin derivative according to any one of embodiments 33-50, wherein position B29 in the parent insulin can be any codable amino acid except Cys, Met, Arg and Lys and the amino acid in position B30 is Lys.
55. The insulin derivative according to any one of embodiments 33-50, wherein the parent insulin has Thr at position B29 and Lys at position B30.
56. The insulin derivative according to any one of embodiments 33-50, wherein the parent insulin is selected from the group consisting of human insulin; des(B1) human insulin; des(B30) human insulin; Gly$^{A21}$ human insulin; Gly$^{A21}$ des(B30) human insulin; Asp$^{B28}$ human insulin; porcine insulin; Lys$^{B28}$Pro$^{B29}$ human insulin; Gly$^{A21}$Arg$^{B31}$Arg$^{B32}$ human insulin; and Lys$^{B3}$Glu$^{B29}$ human insulin.
57. The insulin derivative according to embodiment 33, wherein the insulin derivative is selected from the group consisting of N$^{\epsilon B29}$—(N$^\alpha$—(HOOC(CH$_2$)$_{14}$CO)-γ-Glu) des(B30) human insulin; N$^{\epsilon B29}$—(N$^\alpha$—(HOOC(CH$_2$)$_{15}$CO)-γ-Glu) des(B30) human insulin; N$^{\epsilon B29}$—(N$^\alpha$—(HOOC(CH$_2$)$_{16}$CO)-γ-Glu) des(B30) human insulin; N$^{\epsilon B29}$—(N$^\alpha$—(HOOC(CH$_2$)$_{17}$CO)-γ-Glu) des(B30) human insulin; N$^{\epsilon B29}$—(N$^\alpha$—(HOOC(CH$_2$)$_{18}$CO)-γ-Glu) des(B30) human insulin; N$^{\epsilon B29}$—(N$^\alpha$—(HOOC(CH$_2$)$_{16}$CO)-γ-Glu-N-(γ-Glu)) des(B30) human insulin; N$^{\epsilon B29}$—(N$^\alpha$-(Asp-OC(CH$_2$)$_{16}$CO)-γ-Glu) des(B30) human insulin; N$^{\epsilon B29}$—(N$^\alpha$-(Glu-OC(CH$_2$)$_{14}$CO)-γ-Glu) des(B30) human insulin; N$^{\epsilon B29}$—(N$^\alpha$-(Glu-OC(CH$_2$)$_{14}$CO—) des(B30) human insulin; N$^{\epsilon B29}$—(N$^\alpha$-(Asp-OC(CH$_2$)$_{16}$CO—) des(B30) human insulin; N$^{\epsilon B29}$—(N$^\alpha$—(HOOC(CH$_2$)$_{16}$CO)-α-Glu-N-(β-Asp)) des(B30) human insulin; N$^{\epsilon B29}$—(N$^\alpha$-(Gly-OC(CH$_2$)$_{13}$CO)-γ-Glu) des(B30) human insulin; N$^{\epsilon B29}$—(N$^\alpha$-(Sar-OC(CH$_2$)$_{13}$CO)-γ-Glu) des(B30) human insulin; N$^{\epsilon B29}$—(N$^\alpha$—(HOOC(CH$_2$)$_{13}$CO)-γ-Glu) des(B30) human insulin; (N$^{\epsilon B29}$—(N$^\alpha$—(HOOC(CH$_2$)$_{13}$CO-β-D-Asp) des(B30) human insulin; N$^{\epsilon B29}$—(N$^\alpha$—(HOOC(CH$_2$)$_{13}$CO)-α-Glu) des(B30) human insulin; N$^{\epsilon B29}$—(N$^\alpha$—(HOOC(CH$_2$)$_{16}$CO)-γ-D-Glu) des(B30) human insulin; N$^{\epsilon B29}$—(N$^\alpha$—(HOOC(CH$_2$)$_{14}$CO)-β-D-Asp) des(B30) human insulin; N$^{\epsilon B29}$—(N$^\alpha$—(HOOC(CH$_2$)$_{14}$CO)-β-D-Asp) des(B30) human insulin; N$^{\epsilon B29}$—(N—HOOC(CH$_2$)$_{16}$CO-β-D-Asp) des(B30) human insulin; N$^{\epsilon B29}$—(N—HOOC(CH$_2$)$_{14}$CO-IDA) des(B30) human insulin; N$^{\epsilon B29}$—[N—(HOOC(CH$_2$)$_{16}$CO)—N-(carboxyethyl)-Gly] des(B30) human insulin; N$^{\epsilon B29}$—[N—(HOOC(CH$_2$)$_{14}$CO)—N-(carboxyethyl)-Gly] des(B30) human insulin; and N$^{\epsilon B29}$—[N—(HOOC(CH$_2$)$_{14}$CO)—N-(carboxymethyl)-β-Ala] des(B30) human insulin.
58. The insulin derivative according to embodiment 57, wherein the insulin derivative is N$^{\epsilon B29}$—(N$^\alpha$—(HOOC(CH$_2$)$_{14}$CO)-γ-Glu) des(B30) human insulin.
59. The insulin derivative according to embodiment 57, wherein the insulin derivative is N$^{\epsilon B29}$—(N$^\alpha$—(HOOC(CH$_2$)$_{15}$CO)-γ-Glu) des(B30) human insulin.
60. The insulin derivative according to embodiment 57, wherein the insulin derivative is N$^{\epsilon B29}$—(N$^\alpha$—(HOOC(CH$_2$)$_{16}$CO)-γ-Glu) des(B30) human insulin.
61. The insulin derivative according to embodiment 57, wherein the insulin derivative is N$^{\epsilon B29}$—(N$^\alpha$—(HOOC(CH$_2$)$_{17}$CO)-γ-Glu) des(B30) human insulin.
62. The insulin derivative according to embodiment 57, wherein the insulin derivative is N$^{\epsilon B29}$—(N$^\alpha$—(HOOC(CH$_2$)$_{18}$CO)-γ-Glu) des(B30) human insulin.
63. The insulin derivative according to embodiment 57, wherein the insulin derivative is N$^{\epsilon B29}$—(N$^\alpha$—(HOOC(CH$_2$)$_{16}$CO)-γ-Glu-N-(γ-Glu)) des(B30) human insulin.
64. The insulin derivative according to embodiment 57, wherein the insulin derivative is N$^{\epsilon B29}$—(N$^\alpha$-(Asp-OC(CH$_2$)$_{16}$CO)-γ-Glu) des(B30) human insulin.
65. The insulin derivative according to embodiment 57, wherein the insulin derivative is N$^{\epsilon B29}$—(N$^\alpha$-(Glu-OC(CH$_2$)$_{14}$CO)-γ-Glu) des(B30) human insulin.
66. The insulin derivative according to embodiment 57, wherein the insulin derivative is N$^{\epsilon B29}$—(N$^\alpha$-(Glu-OC(CH$_2$)$_{14}$CO—) des(B30) human insulin.
67. The insulin derivative according to embodiment 57, wherein the insulin derivative is N$^{\epsilon B29}$—(N$^\alpha$-(Asp-OC(CH$_2$)$_{16}$CO—) des(B30) human insulin.
68. The insulin derivative according to embodiment 57, wherein the insulin derivative is N$^{\epsilon B29}$—(N$^\alpha$—(HOOC(CH$_2$)$_{16}$CO)-α-Glu-N-(β-Asp)) des(B30) human insulin.
69. The insulin derivative according to embodiment 57, wherein the insulin derivative is N$^{\epsilon B29}$—(N$^\alpha$-(Gly-OC(CH$_2$)$_{13}$CO)-γ-Glu) des(B30) human insulin.

70. The insulin derivative according to embodiment 57, wherein the insulin derivative is $N^{\epsilon B29}$—($N^\alpha$-(Sar-OC(CH$_2$)$_{13}$CO)-γ-Glu) des(B30) human insulin.
71. The insulin derivative according to embodiment 57, wherein the insulin derivative is $N^{\epsilon B29}$—($N^\alpha$—(HOOC(CH$_2$)$_{13}$CO)-γ-Glu) des(B30) human insulin.
72. The insulin derivative according to embodiment 57, wherein the insulin derivative is ($N^{\epsilon B29}$—($N^\alpha$—(HOOC(CH$_2$)$_{13}$CO)-β-Asp) des(B30) human insulin.
73. The insulin derivative according to embodiment 57, wherein the insulin derivative is $N^{\epsilon B29}$—($N^\alpha$—(HOOC(CH$_2$)$_{13}$CO)-α-Glu) des(B30) human insulin.
74. The insulin derivative according to embodiment 57, wherein the insulin derivative is $N^{\epsilon B29}$—($N^\alpha$—(HOOC(CH$_2$)$_{16}$CO)-γ-D-Glu) des(B30) human insulin.
75. The insulin derivative according to embodiment 57, wherein the insulin derivative is $N^{\epsilon B29}$—($N^\alpha$—(HOOC(CH$_2$)$_{14}$CO)-β-D-Asp) des(B30) human insulin.
76. The insulin derivative according to embodiment 57, wherein the insulin derivative is $N^{\epsilon B29}$—($N^\alpha$—(HOOC(CH$_2$)$_{14}$CO)-β-D-Asp) des(B30) human insulin.
77. The insulin derivative according to embodiment 57, wherein the insulin derivative is $N^{\epsilon B29}$—(N—HOOC(CH$_2$)$_{16}$CO-β-D-Asp) des(B30) human insulin.
78. The insulin derivative according to embodiment 57, wherein the insulin derivative is $N^{\epsilon B29}$—(N—HOOC(CH$_2$)$_{14}$CO-IDA) des(B30) human insulin.
79. The insulin derivative according to embodiment 57, wherein the insulin derivative is $N^{\epsilon B29}$—[N—(HOOC(CH$_2$)$_{16}$CO)—N-(carboxyethyl)-Gly] des(B30) human insulin.
80. The insulin derivative according to embodiment 57, wherein the insulin derivative is $N^{\epsilon B29}$—[N—(HOOC(CH$_2$)$_{14}$CO)—N-(carboxyethyl)-Gly] des(B30) human insulin.
81. The insulin derivative according to embodiment 57, wherein the insulin derivative is $N^{\epsilon B29}$—[N—(HOOC(CH$_2$)$_{14}$CO)—N-(carboxymethyl)-β-Ala] des(B30) human insulin.
82. The insulin derivative according to any one of embodiments 33-57, wherein the insulin derivative is in the form of a zinc complex, wherein each insulin hexamer binds two zinc ions, three zinc ions, four zinc ions, five zinc ions, six zinc ions, seven zinc ions, eight zinc ions, nine zinc ions or ten zinc ions.
83. The insulin derivative according to any one of the preceding embodiments, wherein the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation.
84. The insulin derivative according to embodiment 83, wherein the diabetes mellitus is Type 1 or 2 diabetes.
85. The insulin derivative according to embodiment 83, wherein the diabetes mellitus is Type 2 diabetes, which fails oral anti-diabetic treatment.
86. The insulin derivative according to any one of the preceding embodiments, wherein the naturally occurring insulin, analogue or derivative exhibiting the prolonged profile of action is administered by injection.
87. The insulin derivative according to any one of the preceding embodiments, wherein the insulin derivative is formulated together with a pharmaceutically acceptable carrier and/or vehicle and/or diluent and/or excipient.
88. Use of an insulin derivative of in the preparation of a pharmaceutical composition for treatment of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation, wherein the insulin derivative is as defined in any one of embodiments 1-87.

Formulation of Insulin, Insulin Analogues or Derivatives Thereof

A pharmaceutical composition containing a naturally occurring insulin, an insulin analogue, or a derivative of a naturally occurring insulin or insulin analogue is termed "an insulin composition" herein. In order to exercise the present invention an insulin composition may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin composition nasally or pulmonally, preferably in compositions, powders or liquids, specifically designed for the purpose.

Injectable insulin compositions can be prepared using the conventional techniques of the pharmaceutical industry which involve dissolving and mixing the ingredients as appropriate to give the desired end product. Thus, according to one procedure, a natural insulin, analogue or derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer is typically selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative useful in embodiments of the invention.

In a further embodiment of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19th edition, 1995.

In a further embodiment of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19th edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid), TRIS (2-amino-2-hydroxymethyl-1,3-propandiol), and sodium phosphate.

A composition for nasal administration may, for example, be prepared as described in European Patent No. 272097 (to Novo Nordisk A/S).

Insulin compositions containing can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin, analogue or derivative employed, the age, body weight, physical activity, and diet of the patient, on a possible combination with other drugs, and on the severity of the state to be treated. It is recommended that the dosage regimen be determined for each individual patient by those skilled in the art in a similar way as for known insulin compositions, however taking into consideration the present teachings concerning dosage intervals.

Where expedient, the insulin compositions may be used in combination with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The present invention is further illustrated by the following examples which, however, are not to be construed as limiting the scope of protection.

DEFINITIONS

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues The insulin analogues may be such wherein position 28 of the B chain may be modified from the natural Pro residue to one of Asp, Lys, or Ile. In another embodiment Lys at position B29 is modified to Pro. In one embodiment B30 may be Lys and then B29 can be any codable amino acid except Cys, Met, Arg and Lys.

Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The expression "a codable amino acid" or "a codable amino acid residue" is used to indicate an amino acid or amino acid residue which can be coded for by a triplet ("codon") of nucleotides.

hGlu is homoglutamic acid.
α-Asp is the L-form of —HNCH(CO—)CH$_2$COOH.
β-Asp is the L-form of —HNCH(COOH)CH$_2$CO—.
α-Glu is the L-form of —HNCH(CO—)CH$_2$CH$_2$COOH.
γ-Glu is the L-form of —HNCH(COOH)CH$_2$CH$_2$CO—.
α-hGlu is the L-form of —HNCH(CO—)CH$_2$CH$_2$CH$_2$COOH.
δ-hGlu is the L-form of —HNCH(COOH)CH$_2$CH$_2$CH$_2$CO—.
β-Ala is —NH—CH$_2$—CH$_2$—COOH.
Sar is sarcosine (N-methylglycine).

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

When an insulin derivative according to the invention is stated to be "soluble at physiological pH values" it means that the insulin derivative can be used for preparing injectable insulin compositions that are fully dissolved at physiological pH values. Such favourable solubility may either be due to the inherent properties of the insulin derivative alone or a result of a favourable interaction between the insulin derivative and one or more ingredients contained in the vehicle.

The following abbreviations have been used in the specification and examples:
IDA: Iminodiacetic acid
Sar: Sarcosine (N-methyl-glycine)
Su: succinimidyl=2,5-dioxo-pyrrolidin-1-yl The invention will further be summarized in the following embodiments:

1. A method for treatment a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said naturally occurring insulin, insulin analogue, or derivative exhibits a prolonged profile of action and wherein said dosages are administered at intervals longer than 24 hours.

2. The method according to embodiment 1, wherein said dosages are administered at intervals of at least 36 hours.
3. The method according to embodiment 2, wherein said dosages are administered at intervals of at least 48 hours.
4. The method according to embodiment 3, wherein said dosages are administered at intervals of at least 72 hours.
5. The method according to embodiment 4, wherein said dosages are administered at intervals of at least 96 hours.
6. The method according to embodiment 5, wherein said dosages are administered at intervals of at least 120 hours.
7. The method according to embodiment 6, wherein said dosages are administered at intervals of at least 144 hours.
8. The method according to embodiment 7, wherein said dosages are administered at intervals of at least 168 hours.
9. The method according to any one of the preceding embodiments, wherein said dosages are administered at intervals of at most 336 hours.
10. The method according to any one of the preceding embodiments, wherein said dosages are administered at intervals of at most 312 hours.
11. The method according to any one of the preceding embodiments, wherein said dosages are administered at intervals of at most 288 hours.
12. The method according to any one of the preceding embodiments, wherein said dosages are administered at intervals of at most 264 hours.
13. The method according to any one of the preceding embodiments, wherein said dosages are administered at intervals of at most 240 hours.
14. The method according to any one of the preceding embodiments, wherein said dosages are administered at intervals of at most 216 hours.
15. The method according to any one of the preceding embodiments, wherein said dosages are administered at intervals of at most 192 hours.
16. The method according to any one of the preceding embodiments, wherein said dosages are administered at intervals of at most 168 hours.
17. The method according to any one of the preceding embodiments, wherein the dosages are administered at regular intervals.
18. The method according to embodiment 17, wherein said dosages are administered every second day.
19. The method according to embodiment 17, wherein said dosages are administered every third day.
20. The method according to embodiment 17, wherein said dosages are administered every 4th day.
21. The method according to embodiment 17, wherein said dosages are administered every 5th day.
22. The method according to embodiment 17, wherein said dosages are administered every 6th day.
23. The method according to embodiment 17, wherein said dosages are administered every 7th day.
24. The method according to embodiment 17, wherein said dosages are administered every 14th day
25. The method according to any one of embodiments 1-16, wherein the dosages are administered at fixed weekdays.
26. The method according to embodiment 25, wherein the dosages are administered at 3 fixed weekdays.
27. The method according to embodiment 25, wherein the dosages are administered at 2 fixed weekdays.
28. The method according to embodiment 26 or 27, wherein none of said fixed weekdays are adjacent to each other.
29. The method according to embodiment 27, wherein 2 fixed weekdays are separated by 2 and 3 other weekdays.
30. The method according to any one of the preceding embodiments, wherein administration of the naturally occurring insulin, insulin analogue or derivative exhibiting a prolonged profile of action is supplemented with more frequent administrations of a fast-acting naturally occurring insulin, insulin analogue or derivative and/or administration of a non-insulin anti-diabetic drug.

31. The method according to any one of embodiments 1-29, wherein substantially no other naturally occurring insulin, insulin analogue or derivative of naturally occurring insulin or insulin analogue is administered to said patient.

32. The method according to embodiment 31, wherein administration of the naturally occurring insulin, insulin analogue or derivative exhibiting a prolonged profile of action is supplemented administration of a non-insulin anti-diabetic drug.

33. The method according to any one of the preceding embodiments, wherein is administered a derivative of said naturally occurring insulin or said insulin analogue, wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:

an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:
 —CO—;
 —CH(COOH)C̲O—;
 —N(CH$_2$COOH)CH$_2$C̲O—;
 —N(CH$_2$COOH)CH$_2$CON(CH$_2$COOH)CH$_2$C̲O—;
 —N(CH$_2$CH$_2$COOH)CH$_2$CH$_2$C̲O—;
 —N(CH$_2$CH$_2$COOH)CH$_2$CH$_2$CON(CH$_2$CH$_2$COOH)CH$_2$CH$_2$C̲O—;
 —NHCH(COOH)(CH$_2$)$_4$NHC̲O—;
 —N(CH$_2$CH$_2$COOH)CH$_2$C̲O—; or
 —N(CH$_2$COOH)CH$_2$CH$_2$C̲O—
that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
 —(CH$_2$)$_m$— where m is an integer in the range of 6 to 32;
 a divalent hydrocarbon chain comprising 1, 2 or 3 —CH═CH— groups and a number of —CH$_2$— groups sufficient to give a total number of carbon atoms in the chain in the range of 10 to 32;
 a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
 —COOH;
 —CO-Asp;
 —CO-Glu;
 —CO-Gly;
 —CO-Sar;
 —CH(COOH)$_2$;
 —N(CH$_2$COOH)$_2$;
 —SO$_3$H; or
 —PO$_3$H;
and any Zn$^{2+}$ complexes thereof, provided that when W is a covalent bond and X is —CO—, then Z is different from —COOH.

34. The method according to embodiment 33, wherein side chain —W—X—Y—Z is attached to the α-amino group of the N-terminal amino acid residue of the B chain of the parent insulin.

35. The method according to embodiment 33, wherein side chain —W—X—Y—Z is attached to the α-amino group of a Lys residue present in the B chain of the parent insulin.

36. The method according to any one of embodiments 33-35, wherein W is a covalent bond.

37. The method according to any one of embodiments 33-35, wherein W is an α-amino acid residue having from 4 to 10 carbon atoms.

38. The method according to embodiment 37, wherein W is selected from the group consisting of α-Asp, β-Asp, α-Glu, γ-Glu, α-hGlu and δ-hGlu.

39. The method according to any one of embodiments 33-35, wherein W is a chain composed of two α-amino acid residues of which one has from 4 to 10 carbon atoms and a free carboxylic acid group while the other has from 2 to 11 carbon atoms but no free carboxylic acid group.

40. The method according to embodiment 39, wherein W is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

41. The method according to any one of embodiments 33-35, wherein W is a chain composed of two α-amino acid residues, independently having from 4 to 10 carbon atoms, and both having a free carboxylic acid group.

42. The method according to embodiment 41, wherein W is selected from the group consisting of α-Asp-α-Asp; α-Asp-α-Glu; α-Asp-α-hGlu; α-Asp-β-Asp; α-Asp-β-Glu; α-Asp-β-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-βAsp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-βAsp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

43. The method according to any one of embodiments 33-42, wherein X is —CO— or —CH(COOH)CO—.

44. The method according to any one of embodiments 33-43, wherein X is
—N(CH₂COOH)CH₂CO—;
—N(CH₂COOH)CH₂CON(CH₂COOH)CH₂CO—;
—N(CH₂CH₂COOH)CH₂CH₂CO—;
—N(CH₂CH₂COOH)CH₂CH₂CON(CH₂CH₂COOH)CH₂CH₂CO—
—N(CH₂CH₂COOH)CH₂CO—; or
—N(CH₂COOH)CH₂CH₂CO—.

45. The method according to any one of embodiments 33-44, wherein Y is —(CH₂)$_m$— where m is an integer in the range of from 6 to 32, from 8 to 20, from 12 to 20 or from 12-16.

46. The method according to any one of embodiments 33-45, wherein Z is —COOH.

47. The method according to any one of embodiments 33-45, wherein Z is —CH(COOH)₂.

48. The method according to any one of embodiments 33-45, wherein Z is —N(CH₂COOH)₂.

49. The method according to any one of embodiments 33-45, wherein Z is —SO₃H.

50. The method according to any one of embodiments 33-45, wherein Z is —PO₃H.

51. The method according to any one of embodiments 33-50, wherein the parent insulin has Asn or Gly at position A21.

52. The method according to any one of embodiments 33-50, wherein the parent insulin is a des(B1) analogue.

53. The method according to any one of embodiments 33-50, wherein the parent insulin is a des(B30) analogue.

54. The method according to any one of embodiments 33-50, wherein position B29 in the parent insulin can be any codable amino acid except Cys, Met, Arg and Lys and the amino acid in position B30 is Lys.

55. The method according to any one of embodiments 33-50, wherein the parent insulin has Thr at position B29 and Lys at position B30.

56. The method according to any one of embodiments 33-50, wherein the parent insulin is selected from the group consisting of human insulin; des(B1) human insulin; des(B30) human insulin; Gly$^{A21}$ human insulin; Gly$^{A21}$ des(B30) human insulin; Asp$^{B28}$ human insulin; porcine insulin; Lys$^{B28}$Pro$^{B29}$ human insulin; Gly$^{A21}$Arg$^{B31}$Arg$^{B32}$ human insulin; and Lys$^{B3}$Glu$^{B29}$ human insulin.

57. The method according to embodiment 33, wherein the insulin derivative is selected from the group consisting of N$^{εB29}$—(W—(HOOC(CH₂)₁₄CO)-γ-Glu) des(B30) human insulin; N$^{εB29}$—(N$^α$—(HOOC(CH₂)₁₅CO)-γ-Glu) des(B30) human insulin; N$^{εB29}$—(N$^α$—(HOOC(CH₂)₁₆CO)-γ-Glu) des(B30) human insulin; N$^{εB29}$—(N$^α$—(HOOC(CH₂)₁₇CO)-γ-Glu) des(B30) human insulin; N$^{εB29}$—(N$^α$—(HOOC(CH₂)₁₈CO)-γ-Glu) des(B30) human insulin; N$^{εB29}$—(N$^α$—(HOOC(CH₂)₁₆CO)-γ-Glu-N-(γ-Glu)) des(B30) human insulin; N$^{εB29}$—(N$^α$-(Asp-OC(CH₂)₁₆CO)-γ-Glu) des(B30) human insulin; N$^{εB29}$—(N$^α$-(Glu-OC(CH₂)₁₄CO)-γ-Glu) des(B30) human insulin; N$^{εB29}$—(N$^α$-(Glu-OC(CH₂)₁₄CO—) des(B30) human insulin; N$^{εB29}$—(N$^α$-(Asp-OC(CH₂)₁₆CO—) des(B30) human insulin; N$^{εB29}$—(N$^α$—(HOOC(CH₂)₁₆CO)-α-Glu-N-(β-Asp)) des(B30) human insulin; N$^{εB29}$—(N$^α$-(Gly-OC(CH₂)₁₃CO)-γ-Glu) des(B30) human insulin; N$^{εB29}$—(N$^α$-(Sar-OC(CH₂)₁₃CO)-γ-Glu) des(B30) human insulin; N$^{εB29}$—(N$^α$—(HOOC(CH₂)₁₃CO)-γ-Glu) des(B30) human insulin; (N$^{εB29}$—(N$^α$—(HOOC(CH₂)₁₃CO)-β-Asp) des(B30) human insulin; N$^{εB29}$—(N$^α$—(HOOC(CH₂)₁₃CO)-α-Glu) des(B30) human insulin; N$^{εB29}$—(N$^α$—(HOOC(CH₂)₁₆CO)-γ-D-Glu) des(B30) human insulin; N$^{εB29}$—(N$^α$—(HOOC(CH₂)₁₄CO)-β-Asp) des(B30) human insulin; N$^{εB29}$—(N$^α$—(HOOC(CH₂)₁₄CO)-β-D-Asp) des(B30) human insulin; N$^{εB29}$—(N—HOOC(CH₂)₁₆CO-β-D-Asp) des(B30) human insulin; N$^{εB29}$—(N—HOOC(CH₂)₁₄CO-IDA) des(B30) human insulin; N$^{εB29}$—[N—(HOOC(CH₂)₁₆CO)—N-(carboxyethyl)-Gly] des(B30) human insulin; N$^{εB29}$—[N—(HOOC(CH₂)₁₄CO)—N-(carboxyethyl)-Gly] des(B30) human insulin; and N$^{εB29}$[N—(HOOC(CH₂)₁₄CO)—N-(carboxymethyl)-β-Ala] des(B30) human insulin.

58. The method according to embodiment 57, wherein the insulin derivative is N$^{εB29}$—(N$^α$—(HOOC(CH₂)₁₄CO)-γ-Glu) des(B30) human insulin.

59. The method according to embodiment 57, wherein the insulin derivative is N$^{εB29}$—(N$^α$—(HOOC(CH₂)₁₅CO)-γ-Glu) des(B30) human insulin.

60. The method according to embodiment 57, wherein the insulin derivative is N$^{εB29}$—(N$^α$—(HOOC(CH₂)₁₆CO)-γ-Glu) des(B30) human insulin.

61. The method according to embodiment 57, wherein the insulin derivative is N$^{εB29}$—(N$^α$—(HOOC(CH₂)₁₇CO)-γ-Glu) des(B30) human insulin.

62. The method according to embodiment 57, wherein the insulin derivative is N$^{εB29}$—(N$^α$—(HOOC(CH₂)₁₈CO)-γ-Glu) des(B30) human insulin.

63. The method according to embodiment 57, wherein the insulin derivative is N$^{εB29}$—(N$^α$—(HOOC(CH₂)₁₆CO)-γ-Glu-N-(γ-Glu)) des(B30) human insulin.

64. The method according to pa graph embodiment 57, wherein the insulin derivative is N$^{εB29}$—(N$^α$-(Asp-OC(CH₂)₁₆CO)-γ-Glu) des(B30) human insulin.

65. The method according to embodiment 57, wherein the insulin derivative is N$^{εB29}$—(N$^α$-(Glu-OC(CH₂)₁₄CO)-γ-Glu) des(B30) human insulin.

66. The method according to embodiment 57, wherein the insulin derivative is N$^{εB29}$—(N$^α$-(Glu-OC(CH₂)₁₄CO—) des(B30) human insulin.

67. The method according to embodiment 57, wherein the insulin derivative is N$^{εB29}$—(N$^α$-(Asp-OC(CH₂)₁₆CO—) des(B30) human insulin.

68. The method according to embodiment 57, wherein the insulin derivative is N$^{εB29}$—(N$^α$—(HOOC(CH₂)₁₆CO)-α-Glu-N-(β-Asp)) des(B30) human insulin.

69. The method according to embodiment 57, wherein the insulin derivative is N$^{εB29}$—(N$^α$-(Gly-OC(CH₂)₁₃CO)-γ-Glu) des(B30) human insulin.

70. The method according to embodiment 57, wherein the insulin derivative is N$^{εB29}$—(N$^α$-(Sar-OC(CH₂)₁₃CO)-γ-Glu) des(B30) human insulin.

71. The method according to embodiment 57, wherein the insulin derivative is N$^{εB29}$—(N$^α$—(HOOC(CH₂)₁₃CO)-γ-Glu) des(B30) human insulin.

72. The method according to embodiment 57, wherein the insulin derivative is (N$^{εB29}$—(N$^α$—(HOOC(CH₂)₁₃CO)-β-Asp) des(B30) human insulin.

73. The method according to embodiment 57, wherein the insulin derivative is N$^{εB29}$—(N$^α$—(HOOC(CH₂)₁₃CO)-α-Glu) des(B30) human insulin.

74. The method according to embodiment 57, wherein the insulin derivative is N$^{εB29}$—(N$^α$—(HOOC(CH₂)₁₆CO)-γ-D-Glu) des(B30) human insulin.

75. The method according to embodiment 57, wherein the insulin derivative is N$^{εB29}$—(N$^α$—(HOOC(CH₂)₁₄CO)-β-D-Asp) des(B30) human insulin.

76. N$^{εB29}$—(N$^α$—(HOOC(CH₂)₁₄CO)-β-D-Asp) des(B30) human insulin.

77. The method according to embodiment 57, wherein the insulin derivative is N$^{εB29}$—(N—HOOC(CH₂)₁₆CO-β-D-Asp) des(B30) human insulin.

78. The method according to embodiment 57, wherein the insulin derivative is $N^{\epsilon B29}$—(N—HOOC(CH$_2$)$_{14}$CO-IDA) des(B30) human insulin.

79. The method according to embodiment 57, wherein the insulin derivative is $N^{\epsilon B29}$—[N—(HOOC(CH$_2$)$_{16}$CO)—N-(carboxyethyl)-Gly] des(B30) human insulin.

80. The method according to embodiment 57, wherein the insulin derivative is $N^{\epsilon B29}$—[N—(HOOC(CH$_2$)$_{14}$CO)—N-(carboxyethyl)-Gly] des(B30) human insulin.

81. The method according to embodiment 57, wherein the insulin derivative is $N^{\epsilon B29}$—[N—(HOOC(CH$_2$)$_{14}$CO)—N-(carboxymethyl)-β-Ala] des(B30) human insulin.

82. The method according to any one of embodiments 33-57, wherein the insulin derivative is in the form of a Zinc complex, wherein each insulin hexamer binds two zinc ions, three zinc ions or four zinc ions.

83. The method according to any one of the preceding embodiments, wherein the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation.

84. The method according to embodiment 83, wherein the diabetes mellitus is Type 1 or 2 diabetes.

85. The method according to embodiment 83, wherein the diabetes mellitus is Type 2 diabetes, which fails oral anti-diabetic treatment.

86. The method according to any one of the preceding embodiments, wherein the naturally occurring insulin, analogue or derivative exhibiting the prolonged profile of action is administered by i.m. injection.

87. The method according to any one of the preceding embodiments, wherein the naturally occurring insulin, insulin analogue or derivative is formulated together with a pharmaceutically acceptable carrier and/or vehicle and/or diluent and/or excipient.

88. A naturally occurring insulin, an insulin analogue, or a derivative of a naturally occurring insulin or insulin analogue for use in a method as defined in any one of the preceding embodiments.

89. Use of a naturally occurring insulin, an insulin analogue, or a derivative of a naturally occurring insulin or insulin analogue in the preparation of a pharmaceutical composition for treatment of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation, wherein the treatment is as defined in any one of embodiments 1-87.

EXAMPLES

To indicate the potential of an insulin product to be used less than once daily the duration of action must be sufficiently long in most subjects using the product. An indication of the duration of action in clinical use may be obtained under single dose experimental conditions, the euglycaemic glucose clamp procedure (L. Heinemann and J. H. Anderson-Jr. Measurement of insulin absorption and insulin action. *Diabetes Technol Ther* 6 (5):698-718, 2004), cf. Example 1.

To investigate the clinical effect of an insulin product, a clinical trial has to be conducted under conditions representing the mode of use of the invention. Clinical trials investigating compounds for the treatment of diabetes with the purpose of obtaining approval and registration are subject to guidelines provided by regional authorities (the European guideline serves as an example: Note for Guidance on Clinical Investigations of Medicinal Products in the Treatment of diabetes Mellitus, EMEA, London, 2002).

As an example representing any insulin analogue with sufficiently long duration of action LysB29(Nε-hexadecandioyl-γ-Glu) des(B30) human insulin corresponding to $N^{\epsilon B29}$—($N^{\alpha}$—(HOOC(CH$_2$)$_{14}$CO)-γ-L-Glu) des(B30) human insulin (Example 4 in WO 2005/012347; in the following "LysB29(Nε-hexadecandioyl-γ-Glu) des(B30) human insulin") was investigated with respect to the clinical effect after less than daily injections.

Example 1

Investigating activity profile and duration of action of LysB29(Nε-hexadecandioyl-γ-Glu) des(B30) human insulin.

Methodology

The investigation was performed as a randomised, double-blind, single centre, six-period cross over trial to compare the activity profiles of LysB29(Nε-hexadecandioyl-γ-Glu) des(B30) human insulin and insulin glargine (IGlar) in subjects with type 1 diabetes and type 2 diabetes, respectively.

Subjects were randomised to different sequences of subcutaneous (s.c.) single-dose administration of 10.4 nmol/kg LysB29(Nε-hexadecandioyl-γ-Glu) des(B30) human insulin and 7.2 nmol/kg IGlar in subjects with type 1 diabetes or 14.0 nmol/kg LysB29(Nε-hexadecandioyl-γ-Glu) des(B30) human insulin and 9.6 nmol/kg IGlar in subjects with type 2 diabetes, respectively.

At each dosing visit subjects received a controlled intravenous infusion of glucose and human soluble insulin (Actrapid®) for 4-6 hours prior to trial drug administration in order to keep the blood glucose concentration stable at a level of 90 mg/dL (5.0 mmol/L), i.e. a euglycaemic clamp with a target blood glucose level of 90 mg/dL (5.0 mmol/L) was initiated. The euglycaemic clamp was terminated at 24 hours post-dosing but earlier if blood glucose levels increased to concentrations above 160 mg/dL (8.9 mmol/L) with no glucose infusion during the last 30 min.

During the period from 24 to 30 hours after trial drug administration, subjects remained fasting. If the blood glucose declined to near or below 70 mg/dL (3.9 mmol/L) during this 6-hour period, the subject received one or more 10 g oral carbohydrate administrations.

Blood samples for measurement of serum LysB29(Nε-hexadecandioyl-γ-Glu) des(B30) human insulin/plasma IGlar, and blood glucose were drawn before dosing and for up to 96 hours after dosing.

Standard safety assessments were performed.

Number of Subjects 20 subjects with type 1 diabetes and 18 subjects with type 2 diabetes completed the trial.

Diagnosis and Main Criteria for Inclusion

Men with type 1 diabetes or type 2 diabetes 12 months) aged 18-69 years (inclusive), with glycosylated haemoglobin (HbA$_{1c}$)≤10% and normally treated with insulin (≤1.2 U/kg/day). Subjects with type 1 diabetes should have been treated with insulin ≤12 months and have a body mass index (BMI) of 18-27 kg/m$^2$ (inclusive) and a fasting C-peptide <0.3 nmol/L. Subjects with type 2 diabetes should have been treated with insulin ≥3 months and have a BMI of 22-35 kg/m$^2$ (inclusive) and a fasting C-peptide <1.0 nmol/L.

Test Product, Dose and Mode of Administration

Single doses 10.4 nmol/kg in subjects with type 1 diabetes and 14.0 nmol/kg in subjects with type 2 diabetes) of LysB29(Nε-hexadecandioyl-γ-Glu) des(B30) human insulin, 1200 nmol/mL, 6 Zn2+/6 LysB29(Nε-hexadecandioyl-γ-Glu) des(B30) human insulin, delivered in 1.5 mL cartridges and injected s.c. in the thigh using Becton-Dickinson MicroFine™ syringes (1000 μL) with attached needles (29 G×12.7 mm).

Duration of Treatment

One single dose of LysB29(Nε-hexadecandioyl-γ-Glu) des(B30) human insulin and IGlar were administered at two different occasions at intervals of 7-21 days.

Reference Therapy, Dose and Mode of Administration

Single doses (7.2 nmol/kg in subjects with type 1 diabetes and 9.6 nmol/kg in subjects with type 2 diabetes) of IGlar (Lantus®), 100 IU/mL, 600 nmol/mL delivered in 3.0 mL cartridges and injected s.c. in the thigh using Becton-Dickinson MicroFine™ syringes (1000 μL) with attached needles (29 G×12.7 mm).

Criteria for Evaluation—Efficacy

Pharmacodynamics:

Glucose infusion rate (GIR) during a euglycaemic clamp for 24 hours following trial drug administration.

Blood glucose concentrations.

Number of oral carbohydrate administrations given from 24 to 30 hours post-dose to avoid hypoglycaemia.

Pharmacokinetics:

Serum LysB29(Nε-hexadecandioyl-γ-Glu) des(B30) human insulin/plasma IGlar concentrations for 96 hours following a single dose of either LysB29(Nε-hexadecandioyl-γ-Glu) des(B30) human insulin or IGlar.

Primary Endpoint:

AUCGIR(0-24 h), the area under the concentration-time curve (AUC) of the GIR curve from 0 to 24 hours Key Secondary Endpoints:

Oral Carbohydrate Administration: number of oral carbohydrate administrations to avoid hypoglycaemia during the period from 24 to 30 hours after dosing Pharmacokinetics (tmax (time to maximum concentration), terminal half-life)

Demography of Trial Population

The 20 male subjects with type 1 diabetes and 20 male subjects with type 2 diabetes were aged 37 and 56 years on average, respectively, mean weight was 74 and 93 kg, mean HbA1c was 7.9 and 7.7%, and they had a mean diabetes duration of 21 and 14 years.

Key Results

The AUCGIR(0-24 h) for LysB29(NE-hexadecandioyl-γ-Glu) des(B30) human insulin, did not capture the total insulin action, since pronounced levels of GIR were still present at clamp termination. GIR levels at 24 hours were approximately 3.5 and 2.5 mg/kg/min for both treatments in type 1 and type 2, respectively.

Mean GIRmax was higher for IGlar (5.6 and 4.2 mg/kg/min) than for LysB29(Nε-hexadecandioyl-γ-Glu) des(B30) human insulin (4.1 and 3.1 mg/kg/min), in type 1 and type 2, respectively.

Mean GIR Time to GIRmax was longer for LysB29(Nε-hexadecandioyl-γ-Glu) des(B30) human insulin (13 to 20 hours) than for IGlar (11 to 13 hours) with no apparent difference between the type 1 and type 2 populations The mean number of oral carbohydrate administrations necessary to keep blood glucose above 70 mg/dL (3.9 mmol/L) during the first 6 hours after euglycaemic clamp termination appeared to be higher for LysB29(Nε-hexadecandioyl-γ-Glu) des(B30) human insulin (7.6 and 8.3) than IGlar (6.8 and 4.2) in type 1 and type 2, respectively.

The mean $t_{max}$ was markedly longer for LysB29(Nε-hexadecandioyl-γ-Glu) des(B30) human insulin (19 to 26 hours) than for IGlar (11-13 hours).

The mean terminal half-life was 18 to 19 hours for LysB29(Nε-hexadecandioyl-γ-Glu) des(B30) human insulin and 13 to 25 hours for IGlar and did not differ between LysB29(Nε-hexadecandioyl-γ-Glu) des(B30) human insulin and IGlar in subjects with type 1 diabetes and in subjects with type 2 diabetes.

Key Safety Results

In general, single-dose administration of LysB29(Nε-hexadecandioyl-γ-Glu) des(B30) human insulin and IGlar, respectively, was well tolerated in subjects with type 1 diabetes and in subjects with type 2 diabetes.

Key Conclusions

LysB29(Nε-hexadecandioyl-γ-Glu) des(B30) human insulin appeared to have a more protracted action profile and a longer duration of action compared with IGlar as evidenced by the GIR profile characteristics (later and lower GIRmax and substantial activity present at clamp termination) and the number of carbohydrate administrations necessary to keep blood glucose above 70 mg/dL (3.9 mmol/L) during the first 6 hours after termination of the 24-hour euglycaemic clamp. The conclusions based on activity data (pharmacodynamics) are supported by the pharmacokinetic data.

Example 2

Investigating the clinical effect of LysB29(Nε-hexadecandioyl-γ-Glu) des(B30) human insulin administered Monday, Wednesday and Friday.

Key Methodological Elements and Results

The trial was designed to assess the feasibility, efficacy, safety and tolerability of LysB29(Nε-hexadecandioyl-γ-Glu) des(B30) human insulin for the treatment of subjects with type 2 diabetes three times weekly (Monday, Wednesday, Friday), all in combination with metformin, in subjects with type 2 diabetes failing on oral antidiabetic (OAD) treatment. LysB29(Nε-hexadecandioyl-γ-Glu) des(B30) human insulin (900 nmol/L concentration) was investigated. Due to the long duration of action of LysB29(Nε-hexadecandioyl-γ-Glu) des(B30) human insulin (>24 hours) it was hypothesised that subjects may be sufficiently regulated with three weekly injections in combination with metformin.

Primary Objective

To assess glucose control with respect to HbA1c after 16 weeks of treatment with LysB29(Nε-hexadecandioyl-γ-Glu) des(B30) human insulin three times weekly (Monday, Wednesday, Friday), or insulin glargine once daily, all in combination with metformin in insulin-naïve subjects with type 2 diabetes failing on OAD treatment.

Materials and Methods

The trial was performed in insulin-naïve subjects with type 2 diabetes, previously treated with one or two oral antidiabetic agents: metformin, SU (or other insulin secretagogue e.g. repaglinide, nateglinide), and alpha-glucosidase inhibitors At the beginning of a run-in period all subjects discontinued their current diabetes treatment and initiated a two week uptitration of metformin, followed by a one-week maintenance period. At randomisation, subjects continued on metformin while adding on basal insulin LysB29(Nε- hexadecandioyl-γ-Glu) des(B30) human insulin 3 times weekly or insulin glargine once daily.

A total of 124 subjects with type 2 diabetes, mean age of 54 years, mean duration of diabetes of 6.9 years, mean BMI of 29.5 kg/m², mean FPG of 10.2 mmol/L, and mean $HbA_{1c}$ of 8.7% were randomised (1:1) to receive once-daily LysB29(Nε-hexadecandioyl-γ-Glu) des(B30) human insulin (900 nmol/mL) (62 subjects) or once-daily insulin glargine (62 subjects), both in combination with metformin, for a treatment period of 16 weeks.

Efficacy Results $HbA_{1c}$

Treatment groups were similar with respect to mean changes in $HbA_{1c}$ from baseline to end of treatment (Table 1 and Table 2).

TABLE 1

Mean $HbA_{1c}$ after 16 Weeks of Treatment

| | LysB29(Nε-hexadecandioyl-γ-Glu) des(B30) human insulin 3 Times Weekly | Insulin glargine Once daily |
|---|---|---|
| $HbA_{1c}$ (%) after 16 weeks of treatment[1] | 7.3 | 7.2 |
| Mean Change from Baseline (% points)[1] | −1.45 | −1.50 |

[1]Arithmetic means

TABLE 2

ANOVA of $HbA_{1c}$ after 16 Weeks of Treatment

| | LysB29(Nε-hexadecandioyl-γ-Glu) des(B30) human insulin 3 Times Weekly | Insulin glargine Once daily |
|---|---|---|
| Treatment Difference vs. Insulin Glargine (% points) | 0.10 [−0.22; 0.41] | 0 |

Results from ANOVA model with treatment, country, sex and OAD treatment at screening (3 levels according to stratification) as fixed factors, and age and baseline $HbA_{1c}$ as covariates Hypoglycaemia For both treatment arms, more than 50% of the subjects did not report any hypoglycaemic episodes, cf. table 3. Only one major hypoglycaemic event was reported during the trial.

TABLE 3

Overview of Hypoglycaemia

| | LysB29(Nε-hexadecandioyl-γ-Glu) des(B30) human insulin 3-times weekly | Insulin glargine Once daily |
|---|---|---|
| Number of subjects | 62 | 62 |
| Total Exposure (years) | 18.1 | 17.7 |
| Major | 1 (2%) 1 | 0 (0%) 0 |
| Minor | 13 (21%) 40 | 14 (23%) 20 |
| Symptoms only | 20 (32%) 66 | 15 (24%) 56 |

Hypoglycaemic episodes defined as: major=hypoglycaemic episode where food, glucagon or i.v. glucose had to be administered to the subject by another person because of severe central nervous system dysfunction associated with the hypoglycaemic episode, minor=non-major episode and plasma glucose value below 3.1 mmol/L, symptoms only=non-major episode and plasma glucose value equal to or above 3.1 mmol/L or no value recorded. N: number of subjects, %: percentage of subjects, E: number of events Insulin Dose

TABLE 4

Mean Insulin Dose after 16 Weeks of Treatment

| | LysB29(Nε-hexadecandioyl-γ-Glu) des(B30) human insulin 3-times weekly | Insulin glargine Once daily |
|---|---|---|
| Total Dose (nmol/kg pr injection) | 6.83 | 2.86 |
| Total Dose (nmol/kg/week) | 20.5 | 20 |

Conclusions

In insulin-naïve subjects with type 2 diabetes failing on OAD treatment, 16 weeks treatment with LysB29(Nε-hexadecandioyl-γ-Glu) des(B30) human insulin three times weekly (Monday, Wednesday, Friday) in combination with metformin, resulted in comparable glycaemic control to that observed for insulin glargine given once daily in combination with metformin.

Example 3

Steady State Clamp—Investigating activity profile and duration of action of LysB29(Nε-hexadecandioyl-γ-Glu) des (B30) human insulin.

Methodology

The investigation was performed as a randomised, double-blind, single centre, two-period cross over trial to compare the activity profiles of LysB29(Nε-hexadecandioyl-γ-Glu) des(B30) human insulin and insulin glargine (IGlar) in subjects with type 1 diabetes.

Subjects were randomised to different sequences of subcutaneous (s.c.) multiple-dose once daily administration of LysB29(Nε-hexadecandioyl-γ-Glu) des(B30) human insulin and IGlar. The doses were either 0.57 U/kg or 0.85 U/kg of LysB29(Nε-hexadecandioyl-γ-Glu) des(B30) human insulin and 0.4 U/kg or 0.6 U/kg IGlar. The subjects were treated for 8 days for each dosing period. There was a washout period lasting 10-20 days between the two dosing periods.

At the last day of each dosing period subjects received a controlled intravenous infusion of glucose and human soluble insulin (Actrapid®) for 8-4 hours prior to trial drug administration in order to keep the blood glucose concentration stable at a level of 100 mg/dL (5.5 mmol/L), i.e. a euglycaemic clamp with a target blood glucose level of 100 mg/dL (5.5 mmol/L) was initiated. The euglycaemic clamp was terminated at 42 hours post-dosing but earlier if blood glucose levels increased to concentrations above 200 mg/dL (11.1 mmol/L) with no glucose infusion during the last 30 min.

Blood samples for measurement of serum LysB29(Nε-hexadecandioyl-γ-Glu) des(B30) human insulin/plasma IGlar, and blood glucose were drawn before dosing and for up to 146 hours after dosing.

Standard safety assessments were performed.

Number of Subjects 21 subjects completed the trial.

Diagnosis and Main Criteria for Inclusion

Male or female subjects with type 1 diabetes (≥12 months) aged 18-69 years (inclusive), with glycosylated haemoglobin (HbA$_{1c}$)≤10% and normally treated with insulin (≤1.2 U/kg/day). Subjects should have been treated with insulin ≥12 months and have a body mass index (BMI) of 18-28 kg/m$^2$ (inclusive) and a fasting C-peptide <0.3 nmol/L.

Test Product, Dose and Mode of Administration

Multiple doses of 0.57 U/kg or 0.85 U/kg of LysB29(Nϵ-hexadecandioyl-γ-Glu) des(B30) human insulin, 600 nmol/ml, LysB29(Nϵ-hexadecandioyl-γ-Glu) des(B30) human insulin, delivered in 3 ml FlexPen® (100 DU/ml) cartridge using NovoFine® 30 G, 8 mm needles.

Duration of Treatment

Multiple doses of LysB29(Nϵ-hexadecandioyl-γ-Glu) des(B30) human insulin and IGlar were administered using during two different dosing periods lasting 8 days (optionally +1-5 days) at intervals of 10-20 days.

Reference Therapy, Dose and Mode of Administration

Multiple doses (0.4 U/lg or 0.6 U/kg) of IGlar (Lantus®), 100 IU/mL, 600 nmol/mL delivered in 3.0 mL 3 mL Optiset® cartridges and injected s.c. in the thigh using PenFine® 31 G, 8 mm.

Criteria for Evaluation—Efficacy

Pharmacodynamics:

Glucose infusion rate (GIR) during a euglycaemic clamp for 42 hours during the 8$^{th}$ and last dosing day.

Blood glucose concentrations.

Pharmacokinetics:

Serum LysB29(Nϵ-hexadecandioyl-γ-Glu) des(B30) human insulin/plasma IGlar concentrations for 144 hours following a single dose of either LysB29(Nϵ-hexadecandioyl-γ-Glu) des(B30) human insulin or IGlar.

Primary Endpoint:

AUCGIR(0-24 h), the area under the curve (AUC) of the GIR curve from 0 to 24 hours Key Secondary Endpoints:

Blood glucose level during euglycaemic clamp period

Pharmacokinetics (tmax, terminal half-life)

Demography of Trial Population

The 35 male and 7 female subjects with type 1 diabetes were aged 40 years on average, respectively, mean weight was 75 kg, mean HbA1c was 7.8%, and they had a mean diabetes duration of 21 years.

Key Results

The AUCGIR(0-24 h) for LysB29(NE-hexadecandioyl-γ-Glu) des(B30) human insulin, did not capture the total insulin action, since pronounced levels of GIR were still present at he 24 hour time point. GIR levels at 24 hours were approximately 2.0 and 3.0 mg/kg/min for LysB29(Nϵ-hexadecandioyl-γ-Glu) des(B30) human insulin after the low or high dose, respectively. The corresponding values for insulin glargine were approximately 0.8 and 1.8 mg/kg/min.

Mean GIRmax was higher for IGlar (5.6 and 4.2 mg/kg/min) than for LysB29(Nϵ-hexadecandioyl-γ-Glu) des(B30) human insulin (4.68 and 4.02 mg/kg/min, respectively), after the highest dose but GIRmax was equal after the lower doses (3.07 mg/kg/min).

Mean GIR Time to GIRmax was longer for LysB29(Nϵ-hexadecandioyl-γ-Glu) des(B30) human insulin (13.2 hours and 6.1 for low and high dose respectively) than for IGlar (5.0 and 4.1 hours for low and high dose, respectively)

Mean peak to trough ranges were less for LysB29(Nϵ-hexadecandioyl-γ-Glu) des(B30) human insulin than after insulin glargine. The values were 1.0 and 0.7 mg/kg/min after the low and high dose, respectively. For insulin glargine the corresponding values were 1.6 and 1.1 mg/kg/min.

Average time to loss of glucose control was longer for LysB29(Nϵ-hexadecandioyl-γ-Glu) des(B30) human insulin than for glargine at both dose levels. This occurred after approximately 40 hours after the low LysB29(Nϵ-hexadecandioyl-γ-Glu) des(B30) human insulin dose and no significant loss of glucose control (defined as an increase of blood glucose of more than a 10 mg/dl) was seen at the 42 hours time point after the high LysB29(Nϵ-hexadecandioyl-γ-Glu) des(B30) human insulin dose. After insulin glargine dosing the loss of glucose control occurred after approximately 24 hours and 26 hours when administering the low and high dose, respectively.

The mean time to the maximum concentration (Cmax) was shorter for insulin glargine than for LysB29(Nϵ-hexadecandioyl-γ-Glu) des(B30) human insulin. For insulin glargine the values were 7.2 and 6.4 hours whereas the values for LysB29(Nϵ-hexadecandioyl-γ-Glu) des(B30) human insulin were 9.2 and 10.1 hours after the middle and high dose, respectively.

The mean terminal half-life was 25.2 hours (95% CI 23 to 28 hours) for LysB29(Nϵ-hexadecandioyl-γ-Glu) des(B30) human insulin and 13.9 hours (95% CI 13 to 15) hours for IGlar.

Key Safety Results

In general, multiple-dose administration of LysB29(Nϵ-hexadecandioyl-γ-Glu) des(B30) human insulin and IGlar, respectively, was well tolerated in subjects with type 1 diabetes.

Key Conclusions

Figure 2:
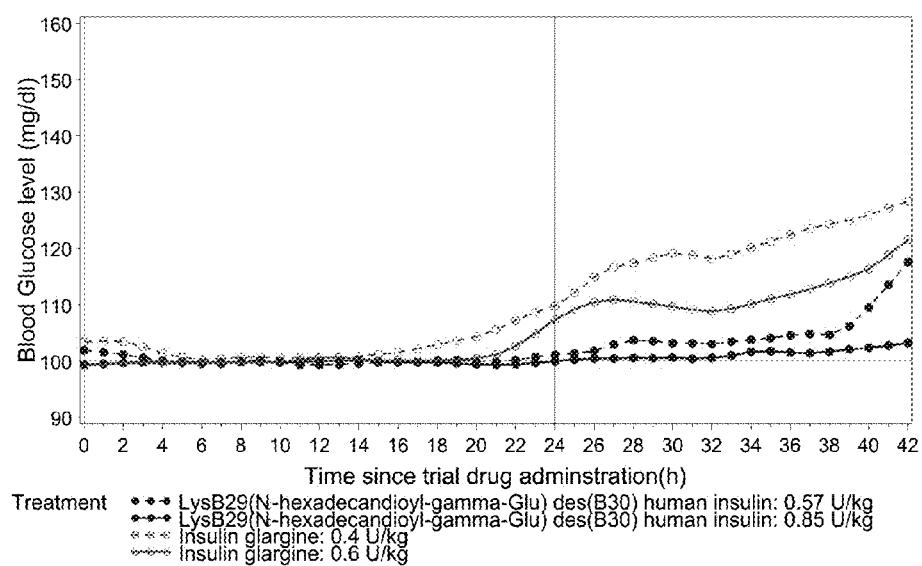
FIG. 2 shows the blood glucose level plotted against the time since the administration of the trial drug.

LysB29(Nϵ-hexadecandioyl-γ-Glu) des(B30) human insulin appeared to have a flatter and more protracted action profile and a longer duration of action compared with IGlar as evidenced by the GIR profile characteristics shown in FIG. 1. The figure shows that LysB29(Nϵ-hexadecandioyl-γ-Glu) des(B30) human insulin has a lower GIRmax at a comparable dose, longer time to GIRmax at both dose levels and less peak to trough range. The duration of action of LysB29(Nϵ-hexadecandioyl-γ-Glu) des(B30) human insulin under the present circumstances was approximately 40 hours or longer as seen in FIG. 2, which shows that LysB29(Nϵ-hexadecandioyl-γ-Glu) des(B30) human insulin has the ability to control blood glucose for a longer period. The conclusions based on activity data (pharmacodynamics) are supported by the pharmacokinetic data (longer time to Cmax and longer terminal half-life).

Example 4

Investigating the clinical effect of LysB29(Nϵ-hexadecandioyl-γ-Glu) des(B30) human insulin administered three times weekly. A trial assessing the number of hypoglycaemic episodes and glycaemic variability during two different regimens (once daily and three times weekly) of LysB29 (Nϵ-hexadecandioyl-γ-Glu) des(B30) human insulin 200 U/ml in subjects with type 1 diabetes.

Key Methodological Elements and Results

The trial was designed to assess the feasibility, safety and tolerability of LysB29(Nϵ-hexadecandioyl-γ-Glu) des(B30) human insulin for the treatment of subjects with type 1 diabetes three times weekly.

The trial was a single centre, double blind, cross-over trial with two in-house treatment periods each consisting of 9 days. LysB29(Nε-hexadecandioyl-γ-Glu) des(B30) human insulin (1200 nmol/L concentration=200 U/ml)) was investigated. Due to the long duration of action of LysB29(Nε-hexadecandioyl-γ-Glu) des(B30) human insulin (>24 hours) it was hypothesised that subjects may be sufficiently regulated with three weekly injections.

Primary Objective

To assess the applicability of LysB29(Nε-hexadecandioyl-γ-Glu) des(B30) human insulin three times weekly, in terms of glycaemic variability, in subjects with type 1 diabetes.

This is done by comparing the number of hypoglycaemic interventions during one week of treatment with LysB29 (Nε-hexadecandioyl-γ-Glu) des(B30) human insulin once daily and three times weekly.

Materials and Methods

The trial was performed in insulin-treated (>12 months prior to the trial) subjects with type 1 diabetes, as diagnosed since ≥12 months. Subjects were randomised to one of two possible treatment sequences with LysB29(Nε-hexadecandioyl-γ-Glu) des(B30) human insulin injected three times weekly and once daily. The two in-house treatment periods were separated by a wash-out period of 5-9 days. The once daily dose of LysB29(Nε-hexadecandioyl-γ-Glu) des(B30) human insulin was fixed during the trial, determined by the individual dose used when entering the trial. When using LysB29(Nε-hexadecandioyl-γ-Glu) des(B30) human insulin tree time a week the dose per injection was one third of the weekly dose obtained during once daily use. The treatment with LysB29(Nε-hexadecandioyl-γ-Glu) des(B30) human insulin was supplemented with insulin Aspart (Novorapid®) for priandial insulin coverage.

Figure 3:
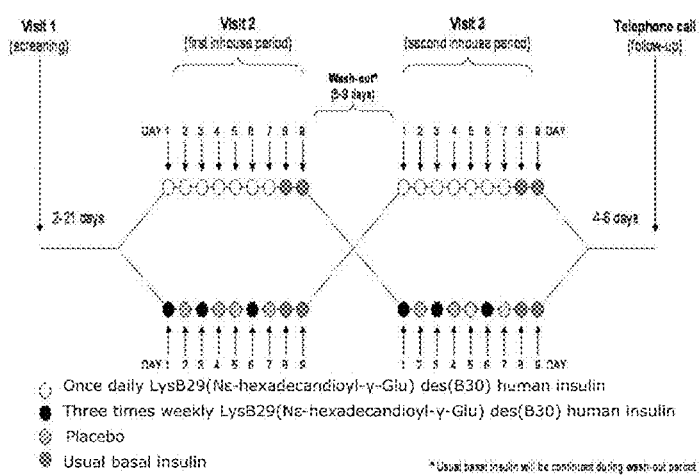
FIG. 3 shows the trial flow.

The plasma glucose levels of the participants were measured on a regular basis by self monitoring procedures. If hypoglycaemia was detected (plasma glucose ≤71 mg/dl) the trial personnel was to ensure the intervention with carbohydrate ingestion until the plasma glucose was stabilised above 71 mg/dl again. The trial flow is shown in FIG. 3.

A total of 18 male subjects with type 1 diabetes, mean age of 43 years, mean duration of diabetes of 18 years, mean BMI of 26 kg/m$^2$, and mean HbA$_{1c}$ of 8.3% were randomised to each treatment sequence (1:1).

Key Results

Hypoglycaemic Events

TABLE 3

Overview of Hypoglycaemic events.

|  | Three times weekly |  |  |  | Once daily |  |  |  |
| --- | --- | --- | --- | --- | --- | --- | --- | --- |
|  | N | (%) | E | R | N | (%) | E | R |
| All Episodes | 17 | (94) | 156 | 1.2 | 17 | (94) | 165 | 1.3 |
| Severe | 0 | (0) | 0 | 0 | 0 | (0) | 0 | 0 |
| Documented Symptomatic | 9 | (50) | 26 | 0.2 | 11 | (61) | 35 | 0.3 |
| Asymptomatic | 17 | (94) | 129 | 1.0 | 17 | (94) | 130 | 1.0 |
| Relative | 1 | (6) | 1 | 0.0 | 0 | (0) | 0 | 0 |
| Probable | 0 | (0) | 0 | 0 | 0 | (0) | 0 | 0 |

N: Number of Subjects, E: Number of Events, R: Number of Events per Day.

Classification of events–Severe=required 3$^{rd}$ party assistance, documented symptomatic=symptoms+plasma glucose<71 mg/dl, Asympptomatic=no symptoms+plasma glucose<71 mg/dl, relative=symptoms+plasma glucose>=71 mg/dl, probable=symptoms+no plasma glucose value.

Plasma Glucose

Fasting plasma glucose was similar after three times weekly and once daily treatment, 8.05 and 7.33 mM, respectively.

Insulin Dose

Total daily bolus insulin doses were similar after three times weekly and once daily treatment, 27.4 and 26.3 U, respectively. The mean variation of the total daily bolus dose from day to day during the three times weekly treatment was larger than during the once daily period, 41.8 and 30.3%, respectively.

CONCLUSIONS

In subjects with type 1 diabetes, 7 days fixed dose treatment with the basal insulin LysB29(Nε-hexadecandioyl-γ-Glu) des(B30) human insulin three times weekly, resulted in no significant difference with regard to the total number of hypoglycaemic events when compared to a fixed dose once daily injection regimen. Fasting plasma glucose and prandial insulin doses (bolus doses) were similar in the two treatment periods, although an 11.5% larger variation in the total daily bolus dose was observed in the three times weekly treatment period. This higher variation was most likely caused by compensatory insulin need due to the difference in basal insulin coverage between the two treatment regimens. Overall, this trial showed that the use of LysB29(Nε-hexadecandioyl-γ-Glu) des(B30) human insulin three times weekly is feasible in subjects with type 1 diabetes.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A method of treating a condition or disease where administration of insulin will be of benefit comprising: administering effective dosages of an insulin derivative to a patient in need thereof, wherein said insulin derivative is administered at intervals of at least 36 hours, wherein the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation, and wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
- an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
- a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
- a covalent bond from X to the α-amino group of the N-terminal amino acid residue of the B chain or to the ε-amino group of a Lys residue present in the B chain of the parent insulin;

X is:
- —CO—;
- —COCH(COOH)CO—;
- —CON(CH$_2$COOH)CH$_2$CO—;
- —CON(CH$_2$COOH)CH$_2$CON(CH$_2$COOH)CH$_2$CO—;
- —CON(CH$_2$CH$_2$COOH)CH$_2$CH$_2$CO—;
- —CON(CH$_2$CH$_2$COOH)CH$_2$CH$_2$CON(CH$_2$CH$_2$COOH)CH$_2$CH$_2$CO—;
- —CONHCH(COOH)(CH$_2$)$_4$NHCO—;
- —CON(CH$_2$CH$_2$COOH)CH$_2$CO—; or
- —CON(CH$_2$COOH)CH$_2$CH$_2$CO— that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
- —(CH$_2$)$_m$— where m is an integer in the range of 6 to 32;
- a divalent hydrocarbon chain comprising 1, 2 or 3 —CH=CH— groups and a number of —CH$_2$— groups sufficient to give a total number of carbon atoms in the chain in the range of 10 to 32;
- a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
- —COOH;
- —CO-Asp;
- —CO-Glu;
- —CO-Gly;
- —CO-Sar;
- —CH(COOH)$_2$;
- —N(CH$_2$COOH)$_2$;
- —SO$_3$H; or
- —PO$_3$H;

and any Zn$^{2+}$ complexes thereof, provided that when W is a covalent bond and X is —CO—, then Z is different from —COOH.

2. The method of claim 1, wherein said dosages are administered at intervals of at least 42 hours, 48 hours, 72 hours or 96 hours.

3. The method of claim 1, wherein the dosages are administered at regular intervals.

4. The method of claim 1, wherein the dosages are administered at fixed weekdays.

5. A method of treating a condition or disease where administration of insulin will be of benefit comprising administering an effective amount of an insulin derivative to a patient in need thereof, wherein said insulin derivative is administered at intervals longer than 36 hours, and wherein the dosages are administered at 3 fixed weekdays.

6. A method of treating a condition or disease where administration of insulin will be of benefit comprising administering an effective amount of an insulin derivative to a patient in need thereof, wherein said insulin derivative is administered at intervals longer than 36 hours, and wherein the dosages are administered at 2 fixed weekdays.

7. The method of claim 1, wherein administration of the insulin derivative exhibiting a prolonged profile of action is supplemented with more frequent administrations of a fast-acting naturally occurring insulin or insulin analogue and/or administration of a non-insulin anti-diabetic drug.

8. The method of claim 1, wherein substantially no other naturally occurring insulin, insulin analogue or derivative of naturally occurring insulin or insulin analogue is administered to said patient.

9. The method of claim 1, wherein the insulin derivative is selected from the group consisting of N$^{εB29}$—(N$^α$—(HOOC(CH$_2$)$_{14}$CO)-γ-Glu) des(B30) human insulin; N$^{εB29}$—(N$^α$—(HOOC(CH$_2$)$_{15}$CO)-γ-Glu) des(B30) human insulin; N$^{εB29}$—(N$^α$—(HOOC(CH$_2$)$_{16}$CO)-γ-Glu) des(B30) human insulin; N$^{εB29}$—(N$^α$—(HOOC(CH$_2$)$_{17}$CO)-γ-Glu) des(B30) human insulin; N$^{εB29}$—(N$^α$—(HOOC(CH$_2$)$_{18}$CO)-γ-Glu) des(B30) human insulin; N$^{εB29}$—(N$^α$—(HOOC(CH$_2$)$_{16}$CO)-γ-Glu-N-(γ-Glu)) des(B30) human insulin; N$^{εB29}$—(N$^α$-(Asp-OC(CH$_2$)$_{16}$CO)-γ-Glu) des(B30) human insulin; N$^{εB29}$—(N$^α$-(Glu-OC(CH$_2$)$_{14}$CO)-γ-Glu) des(B30) human insulin; N$^{εB29}$—(N$^α$-(Glu-OC(CH$_2$)$_{14}$CO—) des(B30) human insulin; N$^{εB29}$—(N$^α$-(Asp-OC(CH$_2$)$_{16}$CO—) des(B30) human insulin; N$^{εB29}$—(N$^α$—(HOOC(CH$_2$)$_{16}$CO)-α-Glu-N-(β-Asp)) des(B30) human insulin; N$^{εB29}$—(N$^α$-(Gly-OC(CH$_2$)$_{13}$CO)-γ-Glu) des(B30) human insulin; N$^{εB29}$—(N$^α$-(Sar-OC(CH$_2$)$_{13}$CO)-γ-Glu) des(B30) human insulin; N$^{εB29}$—(N$^α$—(HOOC(CH$_2$)$_{13}$CO)-γ-Glu) des(B30) human insulin; (N$^{εB29}$—(N$^α$—(HOOC(CH$_2$)$_{13}$CO)-β-Asp) des(B30) human insulin; N$^{εB29}$—(N$^α$—(HOOC(CH$_2$)$_{13}$CO)-α-Glu) des(B30) human insulin; N$^{εB29}$—(N$^α$—(HOOC(CH$_2$)$_{16}$CO)-γ-D-Glu) des(B30) human insulin; N$^{εB29}$—(N$^α$—(HOOC(CH$_2$)$_{14}$CO)-β-D-Asp) des(B30) human insulin; N$^{εB29}$—(N$^α$—(HOOC(CH$_2$)$_{14}$CO)-β-D-Asp) des(B30) human insulin; N$^{εB29}$—(N—HOOC(CH$_2$)$_{16}$CO-β-D-Asp) des(B30) human insulin; N$^{εB29}$—(N—HOOC(CH$_2$)$_{14}$CO—IDA) des(B30) human insulin; N$^{εB29}$—[N—(HOOC(CH$_2$)$_{16}$CO)—N-(carboxyethyl)-Gly] des(B30) human insulin; N$^{εB29}$—[N—(HOOC(CH$_2$)$_{14}$CO)—N-(carboxyethyl)-Gly] des(B30) human insulin; and N$^{εB29}$—[N—(HOOC(CH$_2$)$_{14}$CO)—N-(carboxymethyl)-β-Ala] des(B30) human insulin.

10. The method of claim 1, wherein the insulin derivative is $N^{\epsilon B29}$—($N^{\alpha}$—(HOOC(CH$_2$)$_{14}$CO)-γ-L-Glu) des(B30) human insulin.

11. The method of claim 1, wherein the diabetes mellitus is Type 1 or 2 diabetes.

12. The method of claim 1, wherein the insulin derivative is formulated together with a pharmaceutically acceptable carrier and/or vehicle and/or diluent and/or excipient.

13. The method of claim 1, wherein the condition or disease is selected from the group consisting of diabetes mellitus, hyperglycaemia, pre-diabetes, impaired glucose tolerance, metabolic syndrome, obesity, cachexia, in vivo beta-cell loss/death, excessive appetite, and inflammation, comprising administering the insulin derivative of claim 1.

14. The insulin derivative according to claim 4, wherein the dosages are administered at 3 fixed weekdays.

15. The insulin derivative according to claim 4, wherein the dosages are administered at 2 fixed weekdays.

16. A method of treating diabetes mellitus, hyperglycaemia, pre-diabetes, impaired glucose tolerance, metabolic syndrome, obesity, cachexia, in vivo beta-cell loss/death, excessive appetite, and inflammation, comprising administering to a subject effective dosages of $N^{\epsilon B29}$—($N^{\alpha}$—(HOOC(CH$_2$)$_{14}$CO)-γ-L-Glu) des(B30) human insulin, wherein said dosages are administered at intervals of at least 36 hours.

\* \* \* \* \*

UNITED STATES PATENT AND TRADEMARK OFFICE
CERTIFICATE OF CORRECTION

| | | |
|---|---|---|
| PATENT NO. | : 9,603,904 B2 | Page 1 of 1 |
| APPLICATION NO. | : 13/124750 | |
| DATED | : March 28, 2017 | |
| INVENTOR(S) | : Thue Johansen et al. | |

It is certified that error appears in the above-identified patent and that said Letters Patent is hereby corrected as shown below:

In the Claims

At Column 35, Claim number 1, beginning at Line number 29, please correct as shown below to include underlining in the claim:

X is:
- $-\underline{C}O-$;
- $-CH(COOH)\underline{C}O-$;
- $-N(CH_2COOH)CH_2\underline{C}O-$;
- $-N(CH_2COOH)CH_2CON(CH_2COOH)CH_2\underline{C}O-$;
- $-N(CH_2CH_2COOH)CH_2CH_2\underline{C}O-$;
- $-N(CH_2CH_2COOH)CH_2CH_2CON(CH_2CH_2COOH)CH_2CH_2\underline{C}O-$;
- $-NHCH(COOH)(CH_2)_4NH\underline{C}O-$;
- $-N(CH_2CH_2COOH)CH_2\underline{C}O-$; or
- $-N(CH_2COOH)CH_2CH_2\underline{C}O-$.

Signed and Sealed this
Fourth Day of July, 2017

Joseph Matal
*Performing the Functions and Duties of the
Under Secretary of Commerce for Intellectual Property and
Director of the United States Patent and Trademark Office*